US011039771B1

(12) United States Patent
Pratt et al.

(10) Patent No.: US 11,039,771 B1
(45) Date of Patent: Jun. 22, 2021

(54) APPARATUSES AND METHODS FOR MANAGING TASKS IN ACCORDANCE WITH ALERTNESS LEVELS AND THRESHOLDS

(71) Applicant: AT&T Intellectual Property I, L.P., Atlanta, GA (US)

(72) Inventors: James Pratt, Round Rock, TX (US); Nigel Bradley, Canton, GA (US); Eric Zavesky, Austin, TX (US)

(73) Assignee: AT&T Intellectual Property I, L.P., Atlanta, GA (US)

(*) Notice: Subject to any disclaimer, the term of this patent is extended or adjusted under 35 U.S.C. 154(b) by 0 days.

(21) Appl. No.: 16/807,313

(22) Filed: Mar. 3, 2020

(51) Int. Cl.
| G08B 23/00 | (2006.01) |
| A61B 5/18 | (2006.01) |
| G05D 1/00 | (2006.01) |
| G10L 15/22 | (2006.01) |
| G06N 5/04 | (2006.01) |

(52) U.S. Cl.
CPC ............ *A61B 5/18* (2013.01); *G05D 1/0088* (2013.01); *G06N 5/046* (2013.01); *G10L 15/22* (2013.01); *G10L 2015/225* (2013.01)

(58) Field of Classification Search
CPC ..... A61B 5/18; G10L 15/22; G10L 2015/225; G05D 1/0088; G06N 5/046
See application file for complete search history.

(56) References Cited

U.S. PATENT DOCUMENTS

| 8,566,413 | B2 | 10/2013 | Horvitz |
| 8,630,768 | B2 | 1/2014 | Mcclellan et al. |
| 9,094,539 | B1 | 7/2015 | Noble et al. |
| 9,783,202 | B2 | 10/2017 | Yamada |
| 9,910,435 | B2 | 3/2018 | Sato et al. |
| 10,083,547 | B1 | 9/2018 | Tomatsu |
| 10,137,777 | B2 | 11/2018 | Lu et al. |
| 10,146,221 | B2 | 12/2018 | Funakawa |
| 10,209,708 | B2 | 2/2019 | Hoye |

(Continued)

OTHER PUBLICATIONS

"Affective Automotive AI for Driver Monitoring Systems", affective.com, https://web.archive.org/web/20190403201524/https://www.affectiva.com/product/affectiva-automotive-ai-for-driver-monitoring-solutions/, Apr. 3, 2019, 6 pages.

(Continued)

*Primary Examiner* — Munear T Akki
(74) *Attorney, Agent, or Firm* — Guntin & Gust, PLC; Mark Wilinski

(57) ABSTRACT

Aspects of the subject disclosure may include, for example, obtaining data from a plurality of sensors at a first point in time, analyzing the data to identify a first level of alertness of a user, predicting a second level of alertness that is required by the user to operate a machine at a second point in time that is subsequent to the first point in time, comparing the first level of alertness to the second level of alertness to generate a first comparison result, identifying a first type of a first notification based on the first comparison result, identifying a third point in time to provide the first notification based on the first comparison result, wherein the third point in time is subsequent to the first point in time and prior to the second point in time, and providing the first notification at the third point in time. Other embodiments are disclosed.

20 Claims, 8 Drawing Sheets

(56) References Cited

U.S. PATENT DOCUMENTS

| | | | |
|---|---|---|---|
| 10,290,210 | B2 | 5/2019 | Wolterman |
| 10,295,363 | B1 | 5/2019 | Konrardy et al. |
| 10,331,127 | B2 | 6/2019 | Oba |
| 10,336,321 | B1 | 7/2019 | Fields et al. |
| 10,460,394 | B2 | 10/2019 | Perl et al. |
| 10,471,963 | B2 | 11/2019 | Huang et al. |
| 10,481,602 | B2 | 11/2019 | Chandy |
| 2014/0055274 | A1* | 2/2014 | Hatch ............... G05B 19/4065 340/679 |
| 2017/0066452 | A1 | 3/2017 | Scofield |
| 2017/0316463 | A1 | 11/2017 | Pielot et al. |
| 2018/0326994 | A1 | 11/2018 | Sakai |
| 2019/0129416 | A1 | 5/2019 | Upmanue et al. |
| 2019/0130761 | A1 | 5/2019 | Rau et al. |
| 2019/0143893 | A1 | 5/2019 | Hyuga et al. |
| 2019/0152492 | A1 | 5/2019 | El Kaliouby et al. |
| 2019/0236386 | A1 | 8/2019 | Yu et al. |
| 2019/0276047 | A1* | 9/2019 | Suzuki ............... B60W 50/14 |
| 2019/0366844 | A1* | 12/2019 | Yoon ................... B60K 28/066 |
| 2019/0389381 | A1 | 12/2019 | Pedersen |
| 2019/0389455 | A1* | 12/2019 | Reed .................... B60W 30/09 |
| 2020/0017124 | A1 | 1/2020 | Camhi et al. |
| 2020/0198465 | A1* | 6/2020 | Tanabe ................. B60W 40/08 |

OTHER PUBLICATIONS

"ai-enabled-assistant-robot-will-return-to-the-space-station-with-improved-emotional-intelligence/", https://techcrunch.com/2019/12/05/ai-enabled-assistant-robot-will-return-to-the-space-station-with-improved-emotional-intelligence/, Dec. 5, 2019, 8 pages.

"Driver Behavior Solution & Fleet Safety Management", Nauto, https://www.nauto.com/, available at least as of Feb. 27, 2020, 6 pages.

"Nauto Unveils AI-Powered Driver Behavior Learning Platform for Commercial Fleets", Nauto, https://www.globenewswire.com/news-release/2019/11/06/1942336/0/en/Nauto-Unveils-AI-Powered-Driver-Behavior-Learning-Platform-for-Commercial-Fleets.html, Nov. 6, 2019, 5 pages.

Alberdi, Ane et al., "Towards an automatic early stress recognition system for office environments based on multimodal measurements: A review", Journal of Biomedical Informatics 59 (2016) 49-75, 2016, 27 pages.

Alpert, Ben, "Deep Learning for Distracted Driving Detection", Nauto Engineering, https://www.nauto.com/blog/nauto-engineering-deep-learning-for-distracted-driver-monitoring, Jan. 15, 2019, 4 pages.

Barua, Shaibal, "Intelligent Driver Mental State Monitoring System Using Physiological Sensor Signals", Malardalen University Press Licentiate Theses No. 217, 2015, 88 pages.

Beaulah, Simon et al., "AI in Quality Measurement", Linguamatics Ltd., 2018, 57 pages.

Chen, Lan-Lan et al., "Automatic detection of alertness/drowsiness from physiological signals using wavelet-based nonlinear features and machine learning", Expert Systems with Applications 42 (2015) 7344-7355, 2015, 12 pages.

Collet, Christian et al., "Associating Vehicles Automation With Drivers Functional State Assessment Systems: A Challenge for Road Safety in the Future", ncbi.nlm.nih, Apr. 24, 2019, 22 pages.

De Naurois, Charlotte J. et al., "Detection and prediction of driver drowsiness using artificial neural network models", Accient Analysis & Prevention, vol. 126, May 2019, pp. 95-104.

Fussell, Sidney, "Companies in China Are Using Brain Sensors to Monitor Employees' Emotions", Apr. 30, 2018, 4 pages.

Giannakakis, Giorgos et al., "Stress and anxiety detection using facial cues from videos", Biomedical Signal Processing and Control 31:89-101, Jan. 2017, 13 pages.

Kelion, Leo, "Caterpillar backs eye-tracker to combat driver fatigue", Technology, May 28, 2013, 17 pages.

Meiring, Gys Albertus M. et al., "A Review of Intelligent Driving Style Analysis Systems and Related Artificial Intelligence Algorithms", Dec. 4, 2015, 30 pages.

Ontanon, Santiago, "Learning to Predict Driver Behavior from Observation", The AAAI 2017 Spring Symposium on Learning from Observation of Humans: Technical Report SS-17-06, 2017.

Rahman, Hamidur et al., "Driver monitoring in the Context of Autonomous Vehicle", researchgate.net, Nov. 4, 2015, 10 pages.

Robinson, Bryan, "How Artificial Intelligence is Preventing Cognitive Overload, Compassion Fatigue and Job Burnout", Aug. 23, 2019.

Solanki, Anshita, "Improving worker safety with live fatigue monitoring powered by ML and connected devices", Dec. 28, 2018, 4 pages.

Sonika, "Fatigue Detection Using Voice Analysis", Electronic & Instrumentation Engineering Department, Thapar University, Patiala; Punjab, India, 2015, 73 pages.

Van Der Heiden, Remo M. et al., "Priming Drivers before Handover in Semi-Autonomous Cars", dl.acm.org, May 6, 2017, 13 pages.

* cited by examiner

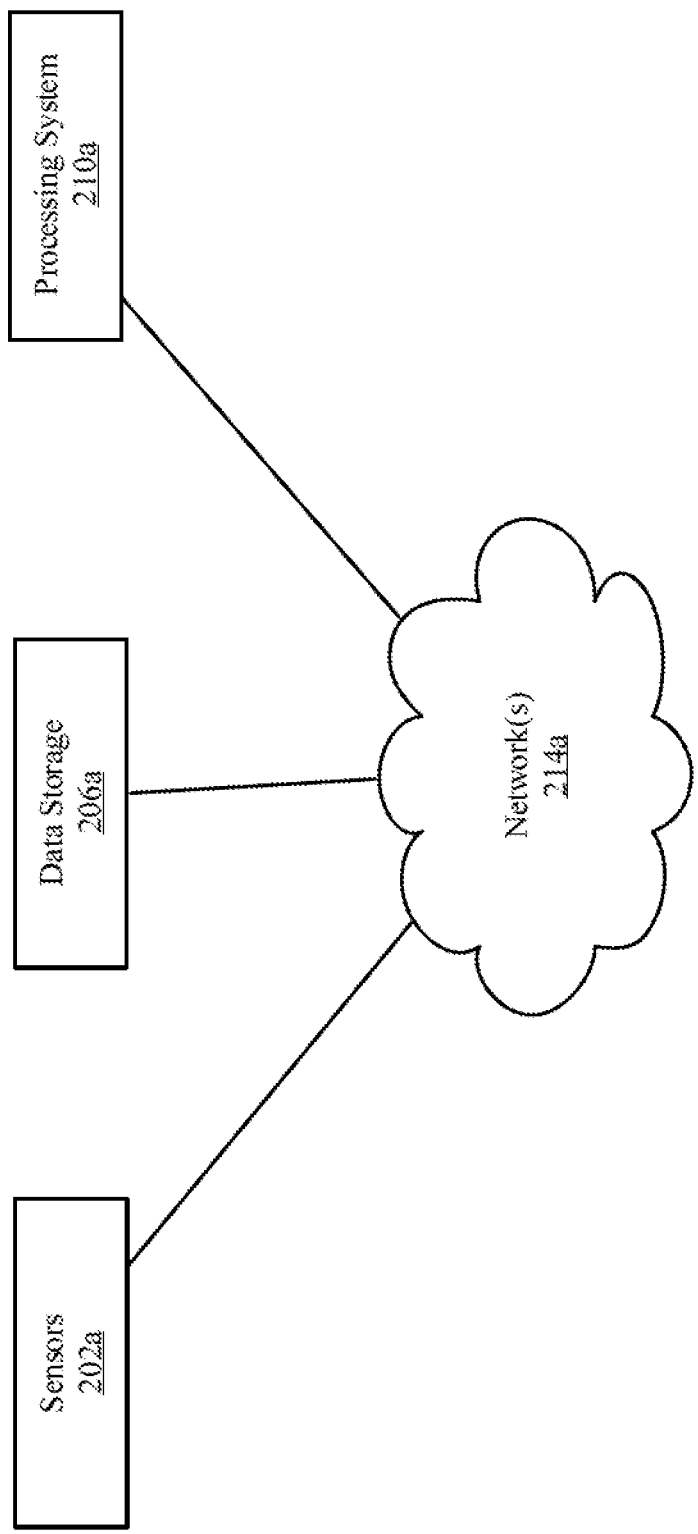

APPARATUSES AND METHODS FOR MANAGING TASKS IN ACCORDANCE WITH ALERTNESS LEVELS AND THRESHOLDS

FIELD OF THE DISCLOSURE

The subject disclosure relates to apparatuses and methods for managing tasks in accordance with alertness levels and thresholds.

BACKGROUND

As the world becomes increasingly connected through communication networks and numerous types of communication devices, additional opportunities are generated for assisting a user of such networks and devices in connection with various tasks. For example, many tasks are being at least partially automated to relive a user of the burden of having to fully perform such tasks. Automation is beginning to take a foothold in connection with machinery, such as for example vehicle/vehicular operations. It is anticipated that vehicular technology will become sufficiently mature to relieve users of the need to "be engaged" behind the wheel/steering column. However, there is likely going to be a phase-in period where the vehicle will generally be able to drive/operate itself, but will at times require user/driver input/assistance to facilitate safe and efficient navigation.

In many applications and environments, users are required to make rapid decisions. Those decisions, and accompanying workload demands, may create a cognitive burden on a user that are not tracked (e.g., by count or frequency). Still further, while there may be opportunities to mitigate the impact of the burden, the mitigation techniques frequently impose additional burdens that must be remembered/tracked/scheduled. Moreover, decision-making processes may be subject to fatigue, where the fatigue may be manifested in one or more forms—e.g., mental fatigue, physical fatigue, group-based workload fatigue [which may be based on social dynamics within a group], etc. In many instances, fatigue may cause a user to become reluctant/hesitant to make a decision, and may increase the time of the user to respond to a particular task or set of inputs, conditions, or events.

BRIEF DESCRIPTION OF THE DRAWINGS

Reference will now be made to the accompanying drawings, which are not necessarily drawn to scale, and wherein:

FIG. 2A is a block diagram illustrating an example, non-limiting embodiment of a system functioning within the communication network of FIG. 1 in accordance with various aspects described herein.

DETAILED DESCRIPTION

Figure 1:
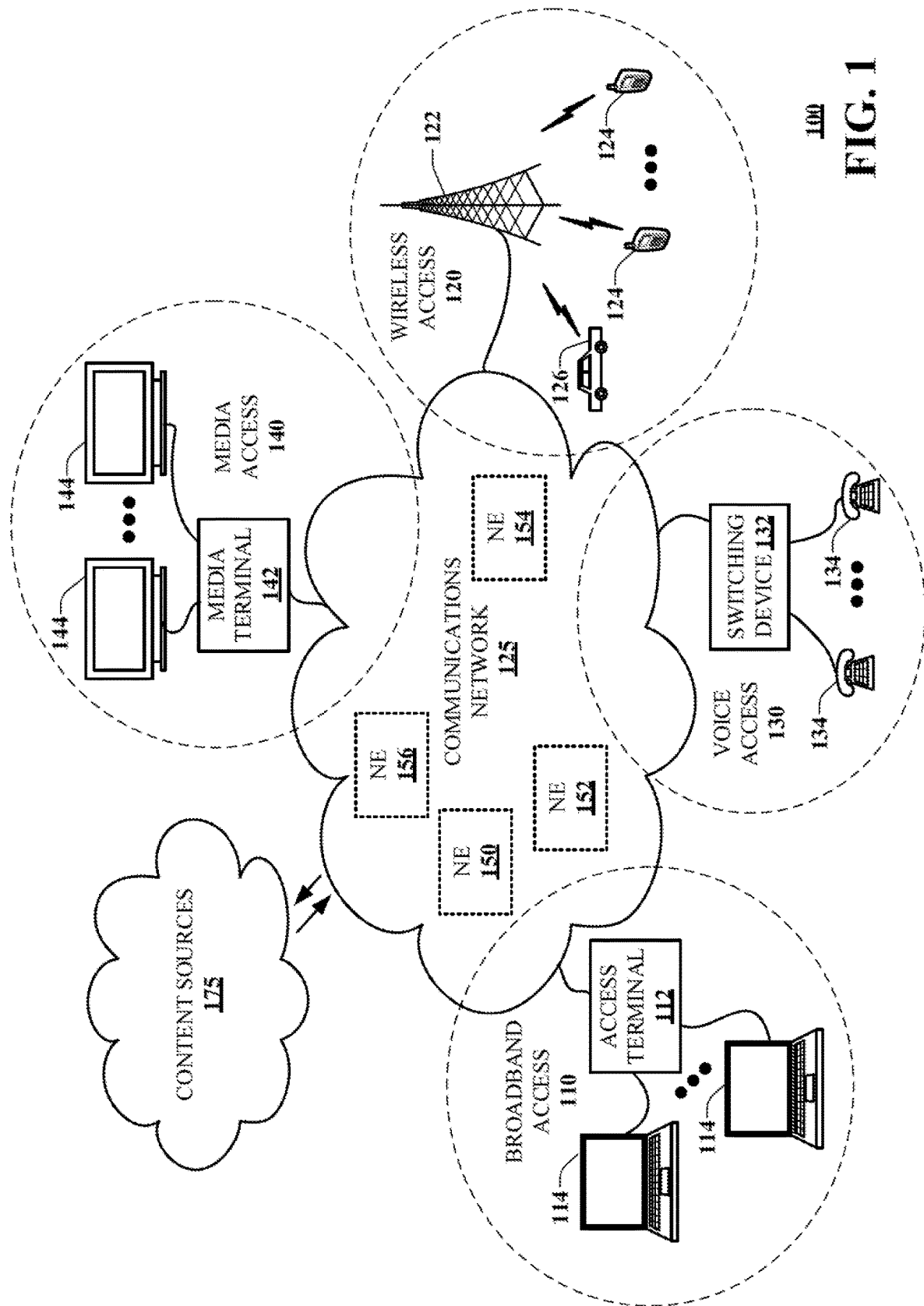
FIG. 1 is a block diagram illustrating an exemplary, non-limiting embodiment of a communications network in accordance with various aspects described herein.

The subject disclosure describes, among other things, illustrative embodiments for facilitating a performance of one or more tasks or operations based on levels of alertness/engagement in respect of one or more thresholds. Other embodiments are described in the subject disclosure.

One or more aspects of the subject disclosure include obtaining data from a plurality of sensors at a first point in time, analyzing the data to identify a first level of alertness of a user, predicting a second level of alertness that is required by the user to operate a machine at a second point in time that is subsequent to the first point in time, comparing the first level of alertness to the second level of alertness to generate a first comparison result, identifying a first type of a first notification based on the first comparison result, identifying a third point in time to provide the first notification based on the first comparison result, wherein the third point in time is subsequent to the first point in time and prior to the second point in time, and providing the first notification at the third point in time.

One or more aspects of the subject disclosure include obtaining data from a plurality of sensors associated with a machine, identifying a first level of alertness of a user of the machine in accordance with the data, predicting a first operation needed of the machine, wherein the first operation occurs subsequent to the identifying of the first level of alertness of the user, resulting in a predicted operation, identifying a second level of alertness required of the user to perform the predicted operation, responsive to determining that the user is insufficiently alert to perform the predicted operation in accordance with the first level of alertness and the second level of alertness: identifying a second operation to be performed in lieu of the first operation or in conjunction with the first operation, and responsive to determining that the user is sufficiently alert to perform the predicted operation in accordance with the first level of alertness and the second level of alertness: identifying a notification to provide to the user, resulting in an identified notification, and providing the identified notification to the user.

One or more aspects of the subject disclosure include obtaining data from a plurality of sensors associated with a primary task at a first point in time, wherein a first user assists in a performance of the primary task, predicting an operation required of the first user to assist in the performance of the primary task at a second point in time that is subsequent to the first point in time, resulting in a predicted operation, determining at a third point in time that is subsequent to the first point in time and prior to the second point in time, that the first user is engaged in the primary task in an amount that is greater than a first threshold, and responsive to the determining that the first user is engaged in the primary task in an amount that is greater than the first threshold: identifying a notification to provide to the first user in relation to the predicted operation, and identifying a fourth point in time that is subsequent to the third point in time and prior to the second point in time, and providing the notification to the first user at the fourth point in time.

Referring now to FIG. 1, a block diagram is shown illustrating an example, non-limiting embodiment of a communications network 100 in accordance with various aspects described herein. For example, communications network 100 can facilitate in whole or in part obtaining data from a plurality of sensors at a first point in time, analyzing the data to identify a first level of alertness of a user, predicting a second level of alertness that is required by the user to operate a machine at a second point in time that is subsequent to the first point in time, comparing the first level of alertness to the second level of alertness to generate a first comparison result, identifying a first type of a first notification based on the first comparison result, identifying a third point in time to provide the first notification based on the first comparison result, wherein the third point in time is subsequent to the first point in time and prior to the second point in time, and providing the first notification at the third point in time. Communications network 100 can facilitate in whole or in part obtaining data from a plurality of sensors associated with a machine, identifying a first level of alertness of a user of the machine in accordance with the data, predicting a first operation needed of the machine, wherein the first operation occurs subsequent to the identifying of the first level of alertness of the user, resulting in a predicted operation, identifying a second level of alertness required of the user to perform the predicted operation, responsive to determining that the user is insufficiently alert to perform the predicted operation in accordance with the first level of alertness and the second level of alertness: identifying a second operation to be performed in lieu of the first operation or in conjunction with the first operation, and responsive to determining that the user is sufficiently alert to perform the predicted operation in accordance with the first level of alertness and the second level of alertness: identifying a notification to provide to the user, resulting in an identified notification, and providing the identified notification to the user. Communications network 100 can facilitate in whole or in part obtaining data from a plurality of sensors associated with a primary task at a first point in time, wherein a first user assists in a performance of the primary task, predicting an operation required of the first user to assist in the performance of the primary task at a second point in time that is subsequent to the first point in time, resulting in a predicted operation, determining at a third point in time that is subsequent to the first point in time and prior to the second point in time, that the first user is engaged in the primary task in an amount that is greater than a first threshold, and responsive to the determining that the first user is engaged in the primary task in an amount that is greater than the first threshold: identifying a notification to provide to the first user in relation to the predicted operation, and identifying a fourth point in time that is subsequent to the third point in time and prior to the second point in time, and providing the notification to the first user at the fourth point in time In particular, in FIG. 1 a communications network 125 is presented for providing broadband access 110 to a plurality of data terminals 114 via access terminal 112, wireless access 120 to a plurality of mobile devices 124 and vehicle 126 via base station or access point 122, voice access 130 to a plurality of telephony devices 134, via switching device 132 and/or media access 140 to a plurality of audio/video display devices 144 via media terminal 142. In addition, communication network 125 is coupled to one or more content sources 175 of audio, video, graphics, text and/or other media. While broadband access 110, wireless access 120, voice access 130 and media access 140 are shown separately, one or more of these forms of access can be combined to provide multiple access services to a single client device (e.g., mobile devices 124 can receive media content via media terminal 142, data terminal 114 can be provided voice access via switching device 132, and so on).

The communications network 125 includes a plurality of network elements (NE) 150, 152, 154, 156, etc. for facilitating the broadband access 110, wireless access 120, voice access 130, media access 140 and/or the distribution of content from content sources 175. The communications network 125 can include a circuit switched or packet switched network, a voice over Internet protocol (VoIP) network, Internet protocol (IP) network, a cable network, a passive or active optical network, a 4G, 5G, or higher generation wireless access network, WIMAX network, UltraWideband network, personal area network or other wireless access network, a broadcast satellite network and/or other communications network.

In various embodiments, the access terminal 112 can include a digital subscriber line access multiplexer (DSLAM), cable modem termination system (CMTS), optical line terminal (OLT) and/or other access terminal. The data terminals 114 can include personal computers, laptop computers, netbook computers, tablets or other computing devices along with digital subscriber line (DSL) modems, data over coax service interface specification (DOCSIS) modems or other cable modems, a wireless modem such as a 4G, 5G, or higher generation modem, an optical modem and/or other access devices.

In various embodiments, the base station or access point 122 can include a 4G, 5G, or higher generation base station, an access point that operates via an 802.11 standard such as 802.11n, 802.11ac or other wireless access terminal. The mobile devices 124 can include mobile phones, e-readers, tablets, phablets, wireless modems, and/or other mobile computing devices.

In various embodiments, the switching device 132 can include a private branch exchange or central office switch, a media services gateway, VoIP gateway or other gateway device and/or other switching device. The telephony devices 134 can include traditional telephones (with or without a terminal adapter), VoIP telephones and/or other telephony devices.

In various embodiments, the media terminal 142 can include a cable head-end or other TV head-end, a satellite receiver, gateway or other media terminal 142. The display devices 144 can include televisions with or without a set top box, personal computers and/or other display devices.

In various embodiments, the content sources 175 include broadcast television and radio sources, video on demand platforms and streaming video and audio services platforms, one or more content data networks, data servers, web servers and other content servers, and/or other sources of media.

In various embodiments, the communications network 125 can include wired, optical and/or wireless links and the network elements 150, 152, 154, 156, etc. can include service switching points, signal transfer points, service control points, network gateways, media distribution hubs, servers, firewalls, routers, edge devices, switches and other network nodes for routing and controlling communications traffic over wired, optical and wireless links as part of the Internet and other public networks as well as one or more private networks, for managing subscriber access, for billing and network management and for supporting other network functions.

Figure 2B:
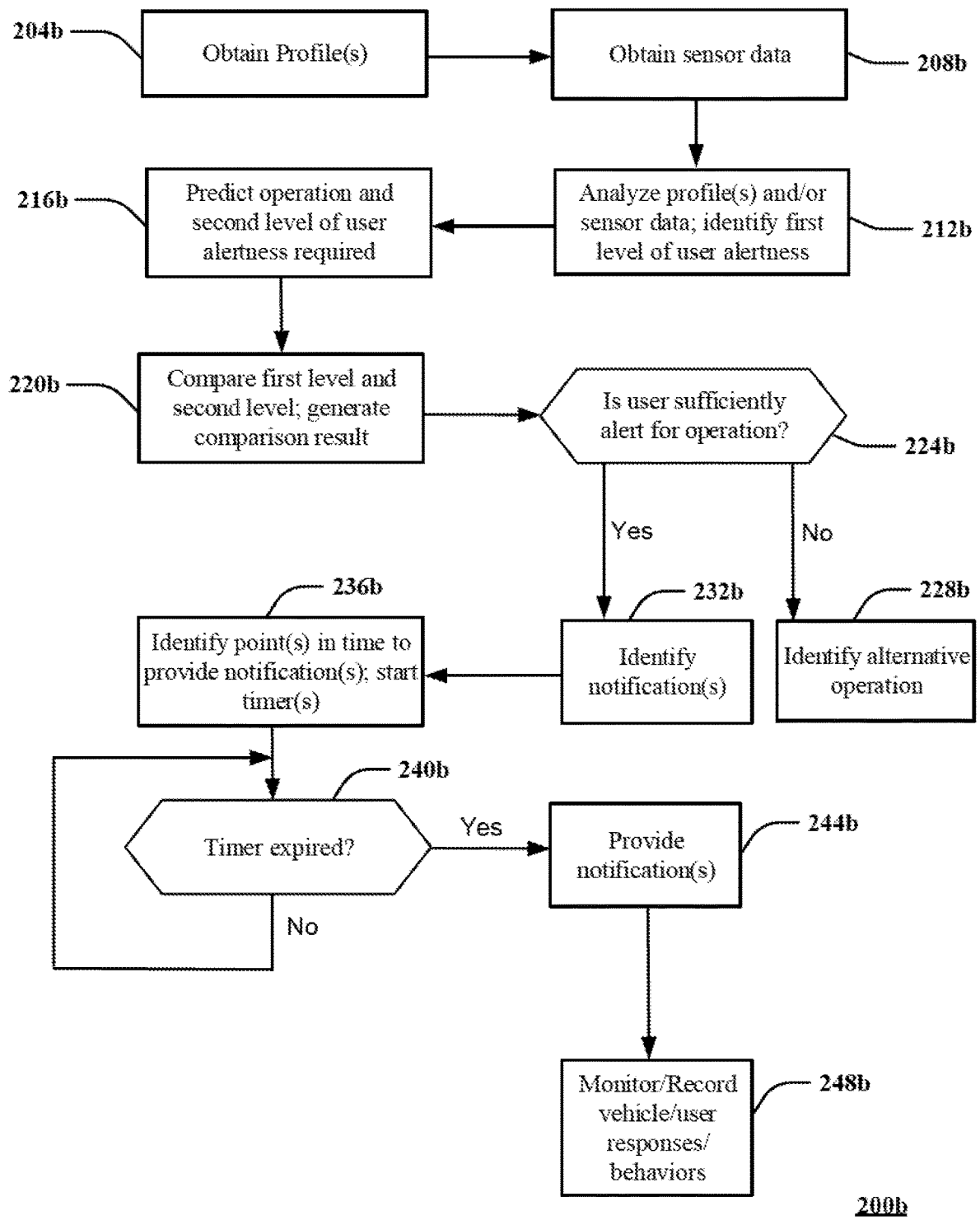
FIG. 2B depicts an illustrative embodiment of a method in accordance with various aspects described herein.

FIG. 2A is a block diagram illustrating an example, non-limiting embodiment of a system 200a functioning within, or operatively overlaid upon, the communication network 100 of FIG. 1 in accordance with various aspects described herein. The system 200a may be used to manage/control aspects of automated and semi-autonomous technologies, such as for example vehicular/vehicle operations. In particular, and as described in further detail below (in relation to the steps/operations that may be performed via a method 200b of FIG. 2B), the system 200a may control/regulate an extent/degree to which a user is requested to perform vehicular operations, identify one or more types/kinds of operations to be performed, and monitor user and vehicle operations/behaviors to facilitate future recommendations/suggestions.

The system 200a may include one or more sensors 202a, a data storage 206a, and a processing system 210a. The sensors 202a may include one or more: temperature sensors, microphones, location-tracking sensors, cameras, gaze-tracking sensors, biometric sensors (e.g., heart rate monitors, perspiration monitors, pulse monitors), etc. The data storage 206a may include, e.g., a database, a memory, a computer-readable/machine-readable medium, etc. The processing system 210a may include one or more processors, potentially organized/arranged as part of a distributed computing environment.

The sensors 202a, the data storage 206a, and the processing system 210a may be communicatively coupled with one another via one or more networks 214a. In some embodiments, in addition to assisting with vehicle operations the networks 214a may facilitate: one or more communication sessions, a transfer/conveyance of data associated with a media presentation, etc.

Referring now to FIG. 2B, an illustrative embodiment of a method 200b in accordance with various aspects described herein is shown. The method 200b may be partially or wholly executed by one or more systems, devices, and/or components, such as for example the systems, devices, and components described herein. For example, and to facilitate ease in description and illustration, operations of the method 200b are described below in relation to the system 200a of FIG. 2A. To demonstrate, aspects of the method 200b may be performed/executed by the processing system 210a of FIG. 2A.

The method 200b may be executed/used to generate one or more recommendations or suggestions regarding machinery, including operations associated with machinery. For example, and as described further below, aspects of the method 200b may control/regulate an allocation of tasks associated with operating a vehicle as between a user (e.g., a driver) and the vehicle. The use of a vehicle in the description of the method 200b that follows is representative of a particular embodiment/use-case; aspects of the method 200b may be applied in connection with other embodiments, including embodiments associated with other types/forms/kinds of machinery/machines.

In block 204b, one or more profiles may be obtained. For example, as part of block 204b, the processing system 210a may obtain one or more profiles from the data storage 206a. The profiles of block 204b may include a profile associated with one or more identifiable/identified users of a vehicle, such as a driver of the vehicle. The profiles of block 204b may include one or more profiles associated with a pool or community of users, where members of the pool/community may, or might not, be known to the user. The profiles of block 204b may include data/parameters/characteristics associated with the vehicle, such as for example an identification of a make and model of the vehicle, service/maintenance records/logs associated with the vehicle, government or manufacturer notices (e.g., recall notices) associated with the vehicle, etc.

The operations of block 204b may be invoked based on a user request. The operations of block 204b may be invoked in response to a user logging-in/signing-in to a navigation assistance application or the like, subscribing to a service, etc. The operations of block 204b may be invoked in response to a user starting the vehicle.

In block 208b, data associated with one or more outputs from the sensors 202a may be obtained. For example, as part of block 208b, the processing system 210a may request (e.g., "pull") the data from the sensors 202a. Alternatively, or additionally, in some embodiments the sensors 202a may provide (e.g., "push") their data to the processing system 210a as soon as the data is available, potentially in accordance with one or more schedules.

In block 212b, the profiles (of block 204b) and/or the sensor outputs/data (of block 208b) may be analyzed to identify a first level of alertness/engagement of a user at a first point in time (e.g., a current point in time). For example, if the sensor outputs/data indicate that an identified user is engaged in a communication session (e.g., a video conference, a voice call, a text message exchange, a discussion amongst fellow occupants in the vehicle, etc.), is engaged in a media presentation (e.g., is watching/listening to a streaming video presentation), etc., a determination may be made as part of block 212b how engaged (or, analogously, disengaged) the identified user is from operating the vehicle. As part of block 212b, a voice/acoustic signature of the identified user (as provided by a sensor 202a) may be compared to voice/signature characteristics of the identified user included in the profiles (as provided by the data storage 206a) to determine the first level of alertness.

In block 216b, a prediction may be made/obtained regarding an operation that may be required of the user to facilitate safe operation/navigation at a second point in time (e.g., a future point in time), and a second level of alertness that may be required of the user to perform that operation. For example, as part of block 216b, a prediction may be made regarding a user's likely path of travel (which may be based at least in part on: a log/record of historical travel/trips of the user as represented in the profiles of block 204b, a calendar of the user, machine learning (ML) and/or artificial intelligence (AI) models, etc.) or other operational decisions the user may be requested to undertake (or verify from automation), and characteristics of the road or area along that path of travel. To demonstrate, and with all other conditions assumed equal, navigation about a hair-pin turn (e.g., a turn characterized by a curvature in an amount that is greater than a threshold) along a dirt road on an inclement weather day may require a greater degree of user alertness/attention/engagement relative to navigation about a substantially straight path along a paved road on a dry, sunny day. Similarly, and again assuming all other conditions being equal, a first area that has historically been prone to accidents may suggest a greater degree of user alertness/attention/engagement is required relative to a second area that has not produced as many accidents.

In some embodiments, the prediction of block 216b may be based in part on the sensor data (of block 208b). For example, in connection with the operation of a vehicle the prediction of block 216b may be based in part on an analysis of image data as captured by, e.g., one or more cameras of the vehicle, cameras located along a road/path, cameras on other vehicles, cameras of communication devices, potentially as shared via one or more messages or social media platforms, etc. In some embodiments, the prediction of block 216b may be based in part on an amount of detected/predicted traffic along a road/path.

In block 220b, the first level (of block 212b) and the second level (of block 216b) may be compared to generate a comparison result. For example, the comparison of block 220b may entail determining/computing a difference between the first level and the second level to generate the comparison result.

In block 224b, a determination may be made, in accordance with the comparison result of block 220b, whether the user is sufficiently alert to perform the operation predicted/identified as part of block 216b. For example, if the second level of block 216b is greater than the first level of block 212b, the user may be (substantially) disengaged from vehicle operations such that it may be risky to request the user to perform the operation of identified in block 216b. In such a scenario, flow may proceed from block 224b to block 228b. Otherwise, if the user is sufficiently alert (e.g., the first level of block 212b is greater than the second level of block 216), flow may proceed from block 224b to block 232b. One or more thresholds may be utilized as part of block 224b.

In block 228b, an alternative operation may be identified. For example, as part of block 228b a route of travel may be modified/changed, e.g., from a first route to a second route that is different from the first route, to avoid the operation identified as part of block 216b. In some embodiments, block 228b may entail identifying other types/kinds of user operations to perform (e.g., requesting that the user engage a brake as opposed to requesting user-operated control of the steering wheel/column). Block 228b may entail a splitting/sharing of the identified operation as between the vehicle and the user (or multiple users, where applicable), where the vehicle may perform part of the identified operation and the user may assist in the performance of another part of the identified operation.

In block 232b, one or more types/kinds of notifications may be identified. The types/kinds of notifications may be based at least in part on the comparison result of block 220b. For example, if the difference between the first level (of block 212b) and the second level (of block 216b) is large (and where the second level is greater than the first level), a first type of notification (e.g., shutting off a presentation of media in the vehicle) may be identified. On the other hand, if the difference between the first level (of block 212b) and the second level (of block 216b) is small (and where the second level is greater than the first level), a second type of notification (e.g., playing a warning message over the vehicle sound system) may be identified. Various types of notifications may be identified as part of block 232b, such as for example vibrating a seat that the user is sitting in, engaging a strobe light (or other light), emitting a scent/fragrance, displaying a message on a display screen, changing a volume or frequency of an output signal associated with audio equipment, etc.

In block 236b, (one or more) third points in time (e.g., a future point in time) may be identified regarding when to generate/provide the notification(s) identified in block 232b. The third point(s) in time may be subsequent to the first point in time (identified in block 212b) and prior to the second point in time (identified in block 216b). The third point(s) in time may be identified in accordance with the comparison result of block 220b. The third point(s) in time may be selected in block 236b in order to ensure that the user is sufficiently engaged (or, analogously, re-engaged) to perform or assist in the operation identified as part of block 216b on the one hand, while at the same time avoiding prematurely taking the user away from/distracting the user from whatever other activities (e.g., consuming a media presentation, engaging in a communication session, internet browsing, e-commerce purchasing activities, sleeping, etc.) the user may otherwise be engaged in at the first point in time. As part of block 236b, one or more timers (e.g., a counter-down timer) may be loaded with a value that corresponds with a difference between the first point in time and the respective third points in time.

In block 240b, a determination may be made regarding whether a given timer of block 236b has expired. If not, flow may remain at block 240b to continue counting down the given timer. Once the given timer has expired, as determined in block 240b, flow may proceed from block 240b to block 244b.

In block 244b, one or more notifications associated with the expired timer(s) of block 240b may be generated/provided. The notification(s) may serve as a stimulus or indicator to the user regarding the nature/identity of the operation to be performed (as identified in block 216b). In some embodiments, a given notification may be targeted/provided to multiple users. For example, providing the given notification to multiple users may provide redundancy, which in turn may increase the likelihood that the notification will be acted on/upon by at least one of the users. Furthermore, in some embodiments, a notification may be targeted to a first user with instructions/directives for the first user to convey the notification to one or more other users. In this manner, it may be more likely that the one or more other users to act on the notification than if the notification was simply provided to the one or more other users.

In block 248b, user and/or vehicle responses/behaviors may be monitored. For example, as part of block 248b an actual amount of time it takes for the user to re-engage in vehicle-based operations may be monitored from the (third) point in time when the notifications are generated/provided as part of block 244b. The user/vehicle operations/behaviors may be recorded (potentially as part of the profile(s): see block 204b). The recording of the user/vehicle operations/behaviors may help facilitate future executions/iterations of the method 200b. Stated slightly differently, the recording of the user/vehicle operations/behaviors in block 248b may incorporate aspects of machine learning (ML) and/or artificial intelligence (AI) to assist the user and/or the vehicle in future operations and decision-making processes based on the information/data/knowledge that is obtained as part of a current execution of the method 200b. In this respect, the method 200b may be incorporated and executed as part of a larger control loop or algorithm that is adaptive to changing conditions, events, inputs, etc.

As described above, different types of sensors may be consulted/interrogated to determine a level of alertness/engagement of a user in respect of operating a vehicle. In some embodiments, one or more of sensors may be included/incorporated as part of the vehicle. One or more of sensors may be included/incorporated as part of a communication device associated with a user. Activities that a user may engage in may be facilitated, in whole or in part, by the vehicle, the communication device, etc., or any combination thereof.

While the method 200b was described above in relation to the operation/use of a vehicle as supported by a user, aspects of the disclosure may be applied in connection with multiple vehicles and multiple users. For example, a decision regarding an operation to be performed by a user or a vehicle might not be made in respect of the user/vehicle taken in isolation, but instead may be based on operations to be performed by other vehicles and/or other users. In this respect, aspects of the disclosure may be used to identify an operation to be performed by a vehicle and/or a user in consideration of other operations to be performed by other vehicles and/or other users.

While some of the examples set forth above pertain to the use and operation of a vehicle (e.g., an automobile, an aircraft [e.g., a plane, a helicopter, a drone, etc.], a satellite, marine craft/a marine vessel, etc.), aspects of this disclosure may be utilized in conjunction with other types/kinds of applications and environments, inclusive of other types of machines. For example, aspects of this disclosure may be utilized in connection with industrial applications (e.g., mining, machining, cutting, printing, etc.), robotics and Internet of Things [IoT] devices (e.g., automation in factories), surveillance via, e.g., remotely operated cameras, drones, etc., medical/clinical procedures, network maintenance activities (e.g., remote component/device repairs, installation, routing configuration, security validation), business activities (e.g., marketing, accounting, operations, etc.), content editing (e.g., search video for suspicious activity, moderation for violence, compliance validation, identifying highlights/interesting points, editing/transcribing notes in a conference), etc.

In some embodiments, an agent (e.g., a software agent) may be deployed across conversational or operational tasks. The agent may observe the state of the tasks and detect anomalies for: a user (or group/set of users), decisions over time, group-based effects/impacts, or any combination thereof. In some embodiments, topics in terms of semantics or inputs in activities or decisions may be collected, pooled, and analyzed for variance across time and/or users. Engagement may be measured and attributed by reaction time, biometrics, and/or topics of relevance. Decisions made by a user (or group/set of users) may be assessed/analyzed for relevance or diversity relative to a general task (e.g., was it appropriate to steer a vehicle 45 degrees in response to a small bump in the road?). In accordance with a task and cognitive load understanding/comprehension, one or more systems, devices, and/or components may propose historical decisions or highlight recommendations/suggestions for utilization in connection with a current task and/or a future task.

Figure 2C:
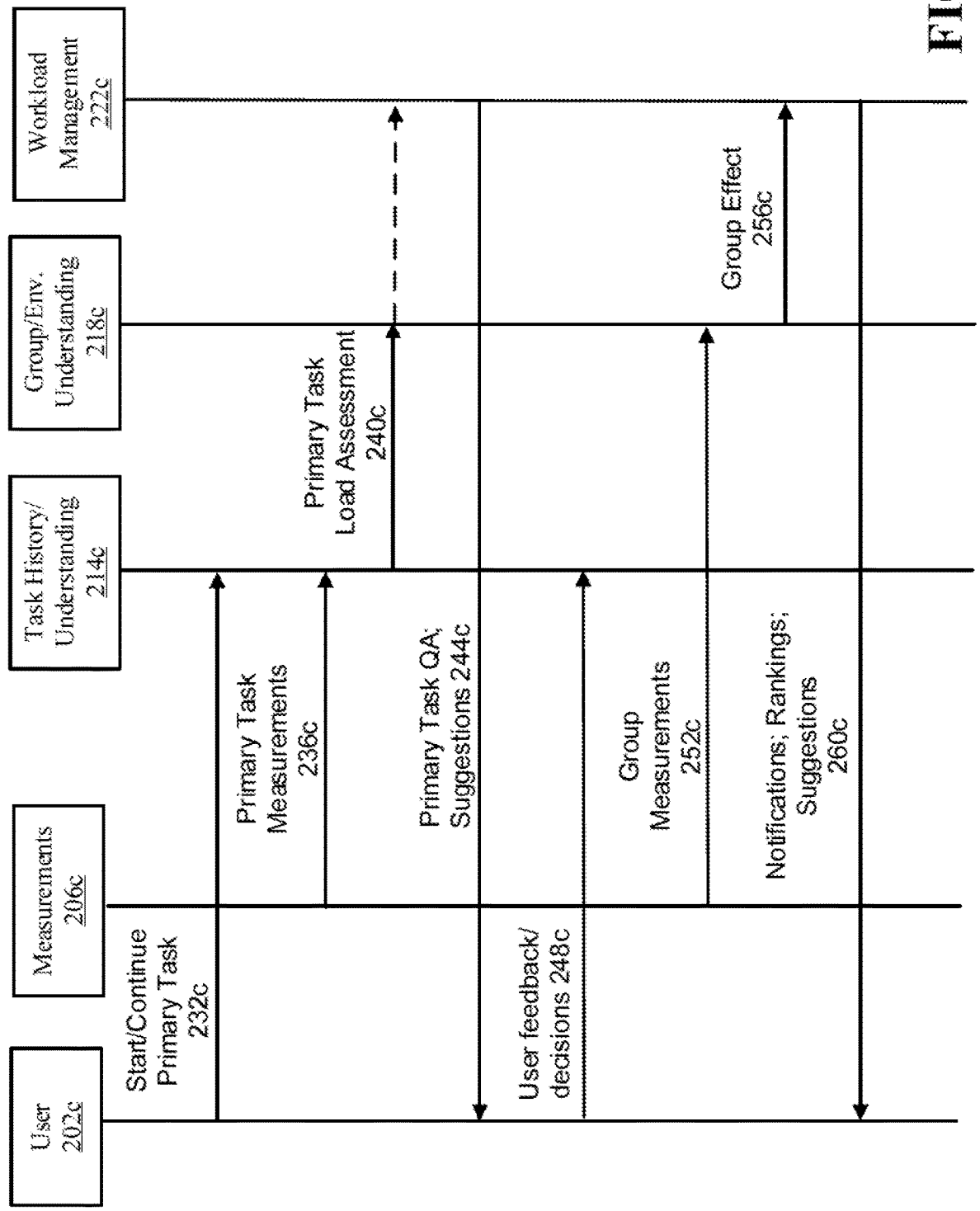
FIG. 2C is a block diagram illustrating an example, non-limiting embodiment of a system functioning within the communication network of FIG. 1 in accordance with various aspects described herein.

Referring now to FIG. 2C, an illustrative embodiment of a system $200c$ in accordance with various aspects of this disclosure is shown. While shown separately, in some embodiments, one or more aspects of the system $200c$ may be combined with one or more aspects of the system 100, the system $200a$, the method $200b$, or any combination thereof. More generally, aspects of the system $200c$ may be implemented in conjunction with aspects of any system, device, or component, such as the systems, devices, and components described herein. In some embodiments, aspects of the system $200c$ may be implemented in conjunction with a machine, such as a vehicle.

The system $200c$ may include a (first) user $202c$, one or more measurements $206c$, a task history/understanding component $214c$, a group/environment understanding component $218c$, and a workload management component $222c$. Each of the user $202c$, the measurements $206c$, the task history/understanding component $214c$, the group/environment understanding components $218c$, and the workload management component $222c$ may be supported by one or more devices (e.g., sensors, processors, communication devices, vehicles, etc.). Furthermore, while described separately, in some embodiments two or more of the entities shown in FIG. 2C (e.g., the task history/understanding component $214c$, the group/environment understanding component $218c$, and the workload management component $222c$) may be located within a common/same housing.

The system $200c$ may be configured to perform and/or facilitate a performance of one or more steps or operations as described in further detail below. For the sake of ease in description, the steps/operations are described in the context of operating a vehicle. One skilled in the art will appreciate that aspects of the steps/operations may be adapted to accommodate other types of applications and environments.

In step $232c$, the user $202c$ may start and/or continue a primary task. For example, and in the context of utilizing a vehicle to navigate from a starting point to a destination, step $232c$ may entail/include starting an engine or a motor of the vehicle. In some embodiments, step $232c$ may include a user entering the destination into a navigation application or the like.

In step 236, one or more measurements associated with the user $202$'s performance of the primary task (of step $232c$) may be obtained. For example, biometric measurements associated with pulse, cortisol, temperature, pupil characteristics (e.g., dilation), etc., may be obtained as part of step 236. As part of step 236, sensors around/about the vehicle may obtain characteristics/parameters in proximity to the vehicle. For example, outputs of collision-avoidance sensors may be obtained as part of step 236.

Information/decisions made by the user $202c$ (which may be identified in conjunction with step $232c$) and the measurements (of step $236c$) may be obtained and processed by the task history/understanding component $214c$. Based on that processing, the task history/understanding component $214c$ may generate and provide a load assessment representative of the cognitive load upon the user $202c$ in conjunction with the performance of the primary task. That primary task load assessment may be provided (e.g., transmitted) to the group/environment understanding component $218c$ and/or the workload management component $222c$ as part of step $240c$.

Based on obtaining (e.g., receiving) the primary task load assessment as part of step $240c$, the workload management component $222c$ may process the load assessment and generate and provide a quality assessment (QA) to the user $202c$ in step $244c$. For example, the QA of step $244c$ may indicate an extent or degree to which the user $202c$ is performing the primary task well (or, analogously, not well). To the extent that any deficiency in the quality of performance is identified/perceived, the workload management component $222c$ may provide recommendations/suggestions to the user $202c$ as part of step $244c$ in an effort to enhance the quality of the user $202c$'s performance or decision-making.

In step $248c$, the task history/understanding component $214c$ may monitor for and/or obtain any user feedback or decisions in respect of the QA/suggestions of step $244c$. In this respect, the user feedback/decisions of step $248c$ may influence future load assessments (see, e.g., step $240c$) by providing an indication of user preferences and/or information/data regarding decision-making processes.

In step $252c$, measurements regarding a group of other users (not shown in FIG. 2C) may be obtained (e.g., received) by the group/environment understanding component $218c$. The group measurements (of step $252c$) may be processed by the group/environment understanding component $218c$ (in conjunction with the primary task load assessment of step $240c$) in step $256c$ to generate an understanding/insight regarding an impact or influence that other users have on the cognitive load on the user 202c. Stated slightly differently, the group effect generated in step 256c recognizes that the load imposed upon the user 202c may be a function of decisions made by others. To illustrate, in the context of operating a vehicle a user (e.g., the user 202c) may make decisions regrading when to brake, accelerate, turn, etc., the vehicle in relation to distances between the vehicle and other vehicles that are nearby.

Based on obtaining the indication of the group effect in step 256c, the workload management component 222c may generate notifications, rankings, and/or suggestions that may be directed to, e.g., the user 202c and/or one or more other users. The notifications, rankings, and/or suggestions may provide information that may be used to mitigate the impact of fatigue that may be experienced by the user 202c and/or one or more other users, such as for example group fatigue of the type frequently experienced on long stretches/spans of highway whereby users/drivers begin to "zone out" despite relative high rates of speed.

Aspects of the system 200c may incorporate profiles associated with a user and/or a vehicle to enhance the accuracy of load assessments and the relevance/applicability of suggestions provided to users, devices, and/or vehicles. In this respect, as additional information or data is obtained the accuracy of outputs of the system 200c and/or the relevance/applicability of the suggestions generated by the system 200c may be more readily accepted/acted upon by users, devices, and vehicles. This may encourage further utilization or adoption, which may further enhance the accuracy and relevance, thereby causing any errors that may otherwise be present to rapidly converge towards zero over time.

While for purposes of simplicity of explanation, the respective processes are shown and described as a series of blocks/operations/steps in FIGS. 2B-2C, it is to be understood and appreciated that the claimed subject matter is not limited by the order of the blocks/operations/steps, as some blocks/operations/steps may occur in different orders and/or concurrently with other blocks/operations/steps from what is depicted and described herein. Moreover, not all illustrated blocks/operations/steps may be required to implement the methods described herein.

Aspects of this disclosure may generate and provide support (e.g., automated support) for continuous decision-making processes. Aspects of the disclosure may help to maintain acceptable levels of workload/user engagement in accordance with one or more predictions. In this respect, aspects of this disclosure may reduce the likelihood of an occurrence of a fault (where a fault may be representative of a poor decision or a bad outcome). Aspects of the disclosure may facilitate concurrent decision quality analyses by allowing/enabling a secondary objective observer to assess decisions and suggest different alternatives throughout a task instead of performing an assessment of an output of the task taken alone.

Aspects of the disclosure may monitor activities/tasks that may be supported/facilitated by multiple users. Aspects of the disclosure may highlight or interject adversarial points to mitigate the impact of group think/group-based fatigue. In this regard, aspects of this disclosure may encourage a refreshed review of alternative options/possibilities by measuring continuity and the repetitive nature of questions/queries and decisions/responses. Aspects of the disclosure may facilitate anonymity by allowing/enabling a first user to suggest an alternative or adversarial point during a discussion while concealing the identity of the first user.

In some embodiments, a prediction of a decision quality may be based in part on state (e.g., an assessment of outputs in accordance with past and/or current inputs) and a task history potentially associated with one or more users. Such predictions may be based on biological and cognitive assessments/analyses.

Aspects of the disclosure may facilitate an efficient deployment of resources, inclusive of automated resources, human resources/capital, etc. Based on an identification of a type of task, an intensity of the task, and/or a timeframe associated with the task, one or more actions may be identified and recommended. For example, if a given task is relatively intense and is scheduled to occur over a long timeframe, a suggestion/recommendation may be directed to a user to take a break at various points interspersed within the timeframe. In this respect, aspects of the disclosure are directed to an understanding of a task and the impact that the task has on the user in terms of duration, intensity, and/or fatigue.

Aspects of this disclosure may modulate fatigue experienced by users by adjusting the influence and contribution that tasks have on users. Feedback generated by users, as well as feedback generated via automation, may inform predictions, changes, suggestions/recommendations, etc., in connection with one or more tasks. In this respect, personalized and/or task-specific guidance/assistance may be generated and provided.

Aspects of the disclosure may be used to detect fatigue in a user (or group/set of users). Such fatigue detection may be facilitated via a monitoring of conversations, topics, changes in cadence, changes in focal detection, etc. Aspects of the disclosure may automate tasks (e.g., automate note taking)) and/or interject other tasks/items (e.g., interject levity, interject historical notes, topics, discussions, etc.) to mitigate/reduce the likelihood and/or impact of potential fatigue.

As described herein, aspects of the disclosure may provide for customized/tailored recommendations/suggestions in respect to a performance of a task. Such customization may take into consideration different behavioral characteristics of a user (e.g., shyness) that may be learned over time. In some embodiments, recommendations/suggestions may be ranked based on time (e.g., recency), user preferences, historical activities or decisions, etc.

Figure 3:
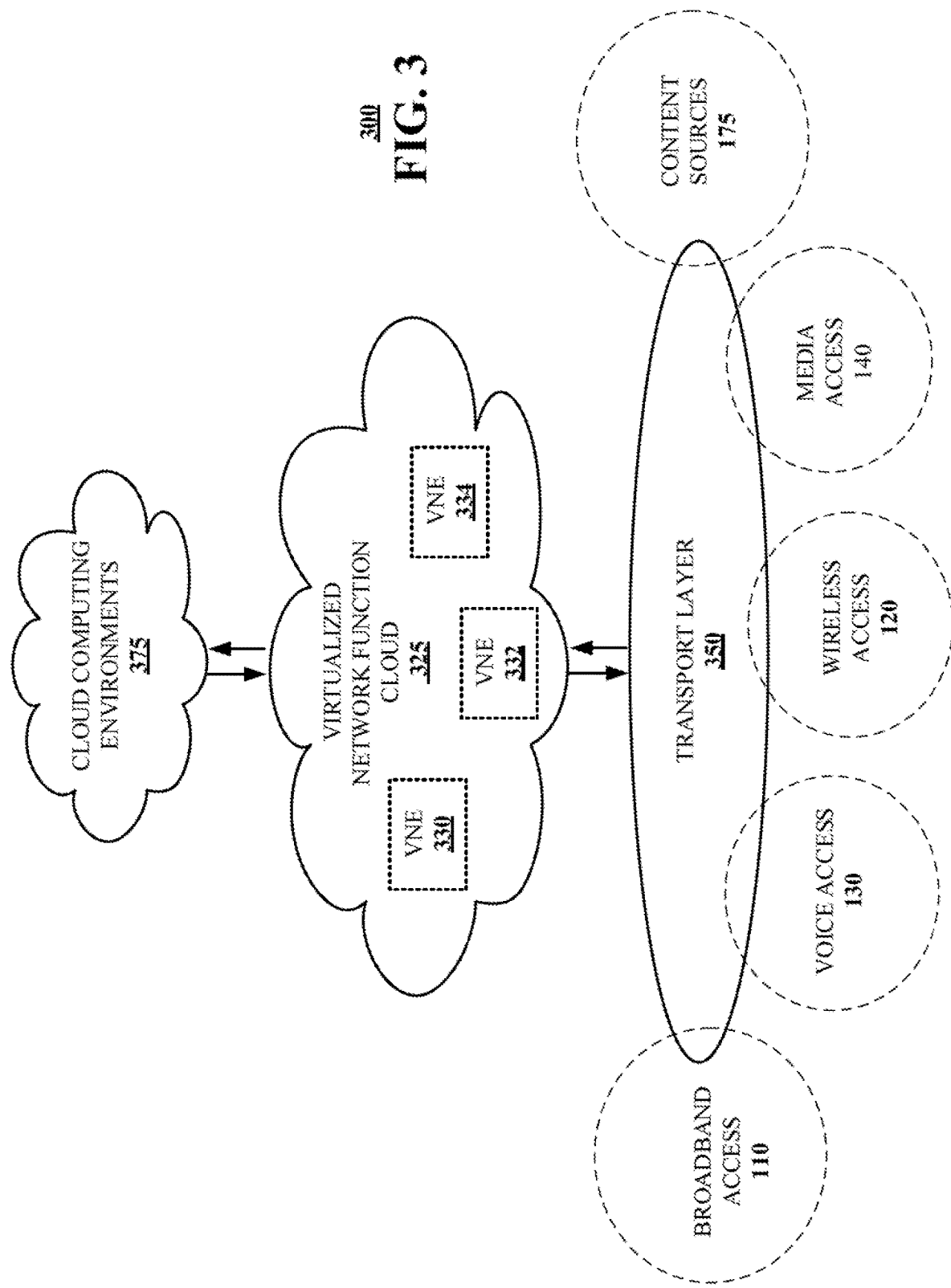
FIG. 3 is a block diagram illustrating an example, non-limiting embodiment of a virtualized communication network in accordance with various aspects described herein.

Referring now to FIG. 3, a block diagram 300 is shown illustrating an example, non-limiting embodiment of a virtualized communication network in accordance with various aspects described herein. In particular, a virtualized communication network is presented that can be used to implement some or all of the subsystems and functions of the communication network 100, the system 200a, the method 200b, and the system 200c presented in FIGS. 1 and 2A-2C. For example, virtualized communication network 300 can facilitate in whole or in part obtaining data from a plurality of sensors at a first point in time, analyzing the data to identify a first level of alertness of a user, predicting a second level of alertness that is required by the user to operate a machine at a second point in time that is subsequent to the first point in time, comparing the first level of alertness to the second level of alertness to generate a first comparison result, identifying a first type of a first notification based on the first comparison result, identifying a third point in time to provide the first notification based on the first comparison result, wherein the third point in time is subsequent to the first point in time and prior to the second point in time, and providing the first notification at the third point in time. Virtualized communication network 300 can facilitate in whole or in part obtaining data from a plurality of sensors associated with a machine, identifying a first level of alertness of a user of the machine in accordance with the data, predicting a first operation needed of the machine, wherein the first operation occurs subsequent to the identifying of the first level of alertness of the user, resulting in a predicted operation, identifying a second level of alertness required of the user to perform the predicted operation, responsive to determining that the user is insufficiently alert to perform the predicted operation in accordance with the first level of alertness and the second level of alertness: identifying a second operation to be performed in lieu of the first operation or in conjunction with the first operation, and responsive to determining that the user is sufficiently alert to perform the predicted operation in accordance with the first level of alertness and the second level of alertness: identifying a notification to provide to the user, resulting in an identified notification, and providing the identified notification to the user. Virtualized communication network 300 can facilitate in whole or in part obtaining data from a plurality of sensors associated with a primary task at a first point in time, wherein a first user assists in a performance of the primary task, predicting an operation required of the first user to assist in the performance of the primary task at a second point in time that is subsequent to the first point in time, resulting in a predicted operation, determining at a third point in time that is subsequent to the first point in time and prior to the second point in time, that the first user is engaged in the primary task in an amount that is greater than a first threshold, and responsive to the determining that the first user is engaged in the primary task in an amount that is greater than the first threshold: identifying a notification to provide to the first user in relation to the predicted operation, and identifying a fourth point in time that is subsequent to the third point in time and prior to the second point in time, and providing the notification to the first user at the fourth point in time In particular, a cloud networking architecture is shown that leverages cloud technologies and supports rapid innovation and scalability via a transport layer 350, a virtualized network function cloud 325 and/or one or more cloud computing environments 375. In various embodiments, this cloud networking architecture is an open architecture that leverages application programming interfaces (APIs); reduces complexity from services and operations; supports more nimble business models; and rapidly and seamlessly scales to meet evolving customer requirements including traffic growth, diversity of traffic types, and diversity of performance and reliability expectations.

In contrast to traditional network elements—which are typically integrated to perform a single function, the virtualized communication network employs virtual network elements (VNEs) 330, 332, 334, etc. that perform some or all of the functions of network elements 150, 152, 154, 156, etc. For example, the network architecture can provide a substrate of networking capability, often called Network Function Virtualization Infrastructure (NFVI) or simply infrastructure that is capable of being directed with software and Software Defined Networking (SDN) protocols to perform a broad variety of network functions and services. This infrastructure can include several types of substrates. The most typical type of substrate being servers that support Network Function Virtualization (NFV), followed by packet forwarding capabilities based on generic computing resources, with specialized network technologies brought to bear when general purpose processors or general purpose integrated circuit devices offered by merchants (referred to herein as merchant silicon) are not appropriate. In this case, communication services can be implemented as cloud-centric workloads.

As an example, a traditional network element 150 (shown in FIG. 1), such as an edge router can be implemented via a VNE 330 composed of NFV software modules, merchant silicon, and associated controllers. The software can be written so that increasing workload consumes incremental resources from a common resource pool, and moreover so that it's elastic: so the resources are only consumed when needed. In a similar fashion, other network elements such as other routers, switches, edge caches, and middle-boxes are instantiated from the common resource pool. Such sharing of infrastructure across a broad set of uses makes planning and growing infrastructure easier to manage.

In an embodiment, the transport layer 350 includes fiber, cable, wired and/or wireless transport elements, network elements and interfaces to provide broadband access 110, wireless access 120, voice access 130, media access 140 and/or access to content sources 175 for distribution of content to any or all of the access technologies. In particular, in some cases a network element needs to be positioned at a specific place, and this allows for less sharing of common infrastructure. Other times, the network elements have specific physical layer adapters that cannot be abstracted or virtualized, and might require special DSP code and analog front-ends (AFEs) that do not lend themselves to implementation as VNEs 330, 332 or 334. These network elements can be included in transport layer 350.

The virtualized network function cloud 325 interfaces with the transport layer 350 to provide the VNEs 330, 332, 334, etc. to provide specific NFVs. In particular, the virtualized network function cloud 325 leverages cloud operations, applications, and architectures to support networking workloads. The virtualized network elements 330, 332 and 334 can employ network function software that provides either a one-for-one mapping of traditional network element function or alternately some combination of network functions designed for cloud computing. For example, VNEs 330, 332 and 334 can include route reflectors, domain name system (DNS) servers, and dynamic host configuration protocol (DHCP) servers, system architecture evolution (SAE) and/or mobility management entity (MME) gateways, broadband network gateways, IP edge routers for IP-VPN, Ethernet and other services, load balancers, distributers and other network elements. Because these elements don't typically need to forward large amounts of traffic, their workload can be distributed across a number of servers—each of which adds a portion of the capability, and overall which creates an elastic function with higher availability than its former monolithic version. These virtual network elements 330, 332, 334, etc. can be instantiated and managed using an orchestration approach similar to those used in cloud compute services.

The cloud computing environments 375 can interface with the virtualized network function cloud 325 via APIs that expose functional capabilities of the VNEs 330, 332, 334, etc. to provide the flexible and expanded capabilities to the virtualized network function cloud 325. In particular, network workloads may have applications distributed across the virtualized network function cloud 325 and cloud computing environment 375 and in the commercial cloud, or might simply orchestrate workloads supported entirely in NFV infrastructure from these third party locations.

Figure 4:
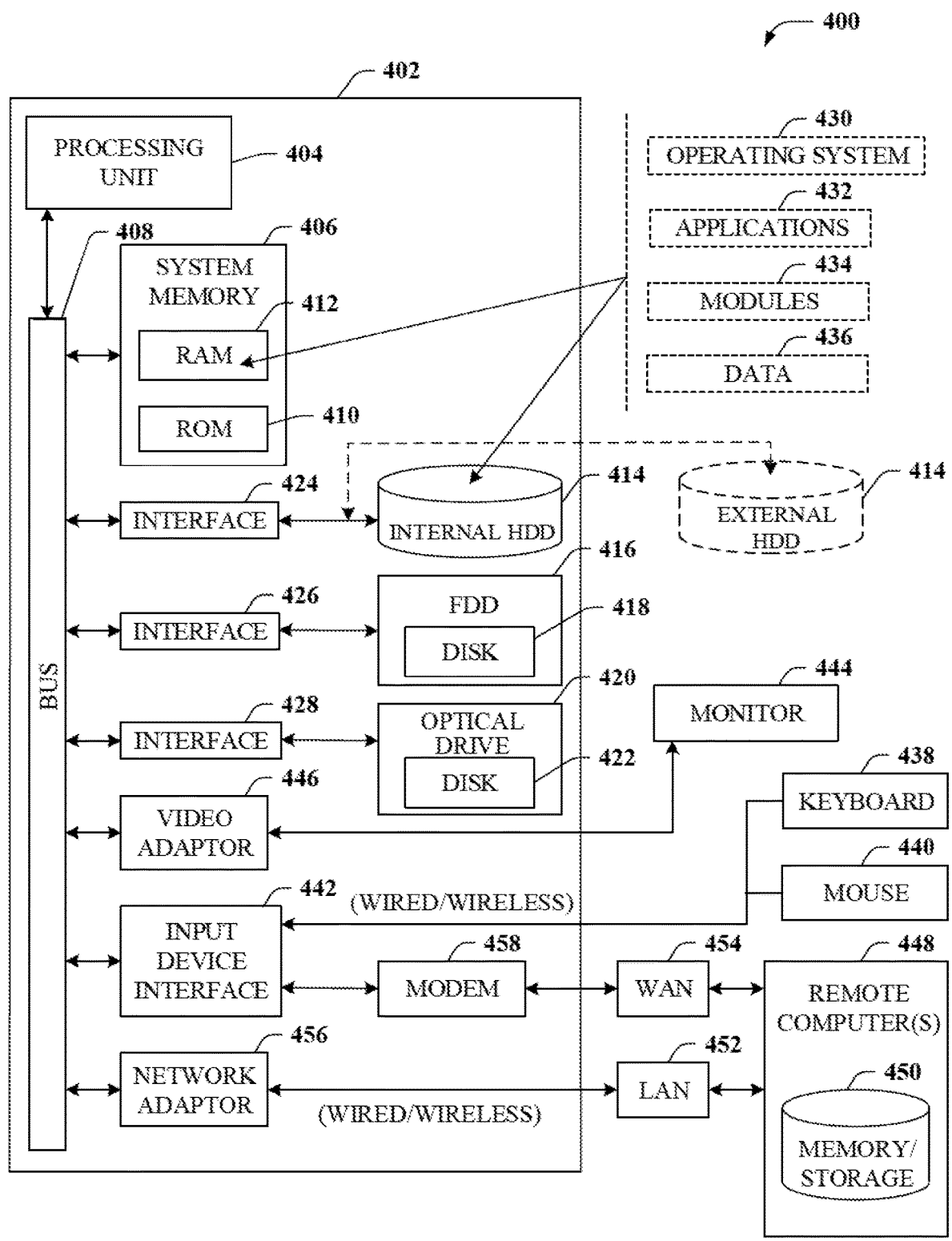
FIG. 4 is a block diagram of an example, non-limiting embodiment of a computing environment in accordance with various aspects described herein.

Turning now to FIG. 4, there is illustrated a block diagram of a computing environment in accordance with various aspects described herein. In order to provide additional context for various embodiments of the embodiments described herein, FIG. 4 and the following discussion are intended to provide a brief, general description of a suitable computing environment 400 in which the various embodiments of the subject disclosure can be implemented. In particular, computing environment 400 can be used in the implementation of network elements 150, 152, 154, 156, access terminal 112, base station or access point 122, switching device 132, media terminal 142, and/or VNEs 330, 332, 334, etc. Each of these devices can be implemented via computer-executable instructions that can run on one or more computers, and/or in combination with other program modules and/or as a combination of hardware and software. For example, computing environment 400 can facilitate in whole or in part obtaining data from a plurality of sensors at a first point in time, analyzing the data to identify a first level of alertness of a user, predicting a second level of alertness that is required by the user to operate a machine at a second point in time that is subsequent to the first point in time, comparing the first level of alertness to the second level of alertness to generate a first comparison result, identifying a first type of a first notification based on the first comparison result, identifying a third point in time to provide the first notification based on the first comparison result, wherein the third point in time is subsequent to the first point in time and prior to the second point in time, and providing the first notification at the third point in time. Computing environment 400 can facilitate in whole or in part obtaining data from a plurality of sensors associated with a machine, identifying a first level of alertness of a user of the machine in accordance with the data, predicting a first operation needed of the machine, wherein the first operation occurs subsequent to the identifying of the first level of alertness of the user, resulting in a predicted operation, identifying a second level of alertness required of the user to perform the predicted operation, responsive to determining that the user is insufficiently alert to perform the predicted operation in accordance with the first level of alertness and the second level of alertness: identifying a second operation to be performed in lieu of the first operation or in conjunction with the first operation, and responsive to determining that the user is sufficiently alert to perform the predicted operation in accordance with the first level of alertness and the second level of alertness: identifying a notification to provide to the user, resulting in an identified notification, and providing the identified notification to the user. Computing environment 400 can facilitate in whole or in part obtaining data from a plurality of sensors associated with a primary task at a first point in time, wherein a first user assists in a performance of the primary task, predicting an operation required of the first user to assist in the performance of the primary task at a second point in time that is subsequent to the first point in time, resulting in a predicted operation, determining at a third point in time that is subsequent to the first point in time and prior to the second point in time, that the first user is engaged in the primary task in an amount that is greater than a first threshold, and responsive to the determining that the first user is engaged in the primary task in an amount that is greater than the first threshold: identifying a notification to provide to the first user in relation to the predicted operation, and identifying a fourth point in time that is subsequent to the third point in time and prior to the second point in time, and providing the notification to the first user at the fourth point in time.

Generally, program modules comprise routines, programs, components, data structures, etc., that perform particular tasks or implement particular abstract data types. Moreover, those skilled in the art will appreciate that the methods can be practiced with other computer system configurations, comprising single-processor or multiprocessor computer systems, minicomputers, mainframe computers, as well as personal computers, hand-held computing devices, microprocessor-based or programmable consumer electronics, and the like, each of which can be operatively coupled to one or more associated devices.

As used herein, a processing circuit includes one or more processors as well as other application specific circuits such as an application specific integrated circuit, digital logic circuit, state machine, programmable gate array or other circuit that processes input signals or data and that produces output signals or data in response thereto. It should be noted that while any functions and features described herein in association with the operation of a processor could likewise be performed by a processing circuit.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically comprise a variety of media, which can comprise computer-readable storage media and/or communications media, which two terms are used herein differently from one another as follows. Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data or unstructured data.

Computer-readable storage media can comprise, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage or other magnetic storage devices or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

With reference again to FIG. 4, the example environment can comprise a computer 402, the computer 402 comprising a processing unit 404, a system memory 406 and a system bus 408. The system bus 408 couples system components including, but not limited to, the system memory 406 to the processing unit 404. The processing unit 404 can be any of various commercially available processors. Dual microprocessors and other multiprocessor architectures can also be employed as the processing unit 404.

The system bus 408 can be any of several types of bus structure that can further interconnect to a memory bus (with or without a memory controller), a peripheral bus, and a local bus using any of a variety of commercially available bus architectures. The system memory 406 comprises ROM 410 and RAM 412. A basic input/output system (BIOS) can be stored in a non-volatile memory such as ROM, erasable programmable read only memory (EPROM), EEPROM, which BIOS contains the basic routines that help to transfer information between elements within the computer 402, such as during startup. The RAM 412 can also comprise a high-speed RAM such as static RAM for caching data.

The computer 402 further comprises an internal hard disk drive (HDD) 414 (e.g., EIDE, SATA), which internal HDD 414 can also be configured for external use in a suitable chassis (not shown), a magnetic floppy disk drive (FDD) 416, (e.g., to read from or write to a removable diskette 418) and an optical disk drive 420, (e.g., reading a CD-ROM disk 422 or, to read from or write to other high capacity optical media such as the DVD). The HDD 414, magnetic FDD 416 and optical disk drive 420 can be connected to the system bus 408 by a hard disk drive interface 424, a magnetic disk drive interface 426 and an optical drive interface 428, respectively. The hard disk drive interface 424 for external drive implementations comprises at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 402, the drives and storage media accommodate the storage of any data in a suitable digital format. Although the description of computer-readable storage media above refers to a hard disk drive (HDD), a removable magnetic diskette, and a removable optical media such as a CD or DVD, it should be appreciated by those skilled in the art that other types of storage media which are readable by a computer, such as zip drives, magnetic cassettes, flash memory cards, cartridges, and the like, can also be used in the example operating environment, and further, that any such storage media can contain computer-executable instructions for performing the methods described herein.

A number of program modules can be stored in the drives and RAM 412, comprising an operating system 430, one or more application programs 432, other program modules 434 and program data 436. All or portions of the operating system, applications, modules, and/or data can also be cached in the RAM 412. The systems and methods described herein can be implemented utilizing various commercially available operating systems or combinations of operating systems.

A user can enter commands and information into the computer 402 through one or more wired/wireless input devices, e.g., a keyboard 438 and a pointing device, such as a mouse 440. Other input devices (not shown) can comprise a microphone, an infrared (IR) remote control, a joystick, a game pad, a stylus pen, touch screen or the like. These and other input devices are often connected to the processing unit 404 through an input device interface 442 that can be coupled to the system bus 408, but can be connected by other interfaces, such as a parallel port, an IEEE 1394 serial port, a game port, a universal serial bus (USB) port, an IR interface, etc.

A monitor 444 or other type of display device can be also connected to the system bus 408 via an interface, such as a video adapter 446. It will also be appreciated that in alternative embodiments, a monitor 444 can also be any display device (e.g., another computer having a display, a smart phone, a tablet computer, etc.) for receiving display information associated with computer 402 via any communication means, including via the Internet and cloud-based networks. In addition to the monitor 444, a computer typically comprises other peripheral output devices (not shown), such as speakers, printers, etc.

The computer 402 can operate in a networked environment using logical connections via wired and/or wireless communications to one or more remote computers, such as a remote computer(s) 448. The remote computer(s) 448 can be a workstation, a server computer, a router, a personal computer, portable computer, microprocessor-based entertainment appliance, a peer device or other common network node, and typically comprises many or all of the elements described relative to the computer 402, although, for purposes of brevity, only a remote memory/storage device 450 is illustrated. The logical connections depicted comprise wired/wireless connectivity to a local area network (LAN) 452 and/or larger networks, e.g., a wide area network (WAN) 454. Such LAN and WAN networking environments are commonplace in offices and companies, and facilitate enterprise-wide computer networks, such as intranets, all of which can connect to a global communications network, e.g., the Internet.

When used in a LAN networking environment, the computer 402 can be connected to the LAN 452 through a wired and/or wireless communication network interface or adapter 456. The adapter 456 can facilitate wired or wireless communication to the LAN 452, which can also comprise a wireless AP disposed thereon for communicating with the adapter 456.

When used in a WAN networking environment, the computer 402 can comprise a modem 458 or can be connected to a communications server on the WAN 454 or has other means for establishing communications over the WAN 454, such as by way of the Internet. The modem 458, which can be internal or external and a wired or wireless device, can be connected to the system bus 408 via the input device interface 442. In a networked environment, program modules depicted relative to the computer 402 or portions thereof, can be stored in the remote memory/storage device 450. It will be appreciated that the network connections shown are example and other means of establishing a communications link between the computers can be used.

The computer 402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This can comprise Wireless Fidelity (Wi-Fi) and BLUETOOTH® wireless technologies. Thus, the communication can be a predefined structure as with a conventional network or simply an ad hoc communication between at least two devices.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, ac, ag, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands for example or with products that contain both bands (dual band), so the networks can provide real-world performance similar to the basic 10BaseT wired Ethernet networks used in many offices.

Figure 5:
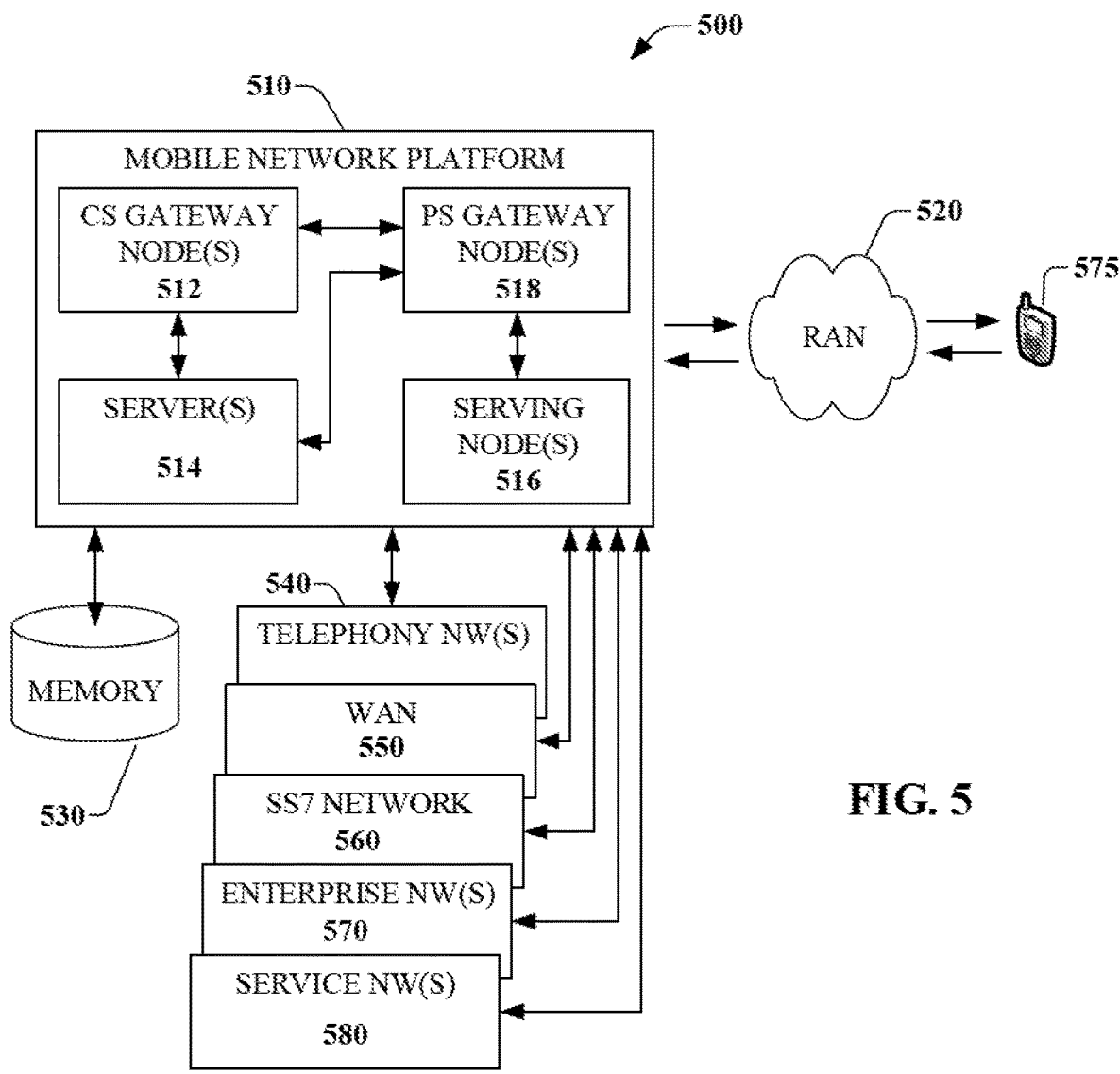
FIG. 5 is a block diagram of an example, non-limiting embodiment of a mobile network platform in accordance with various aspects described herein.

Turning now to FIG. 5, an embodiment 500 of a mobile network platform 510 is shown that is an example of network elements 150, 152, 154, 156, and/or VNEs 330, 332, 334, etc. For example, platform 510 can facilitate in whole or in part obtaining data from a plurality of sensors at a first point in time, analyzing the data to identify a first level of alertness of a user, predicting a second level of alertness that is required by the user to operate a machine at a second point in time that is subsequent to the first point in time, comparing the first level of alertness to the second level of alertness to generate a first comparison result, identifying a first type of a first notification based on the first comparison result, identifying a third point in time to provide the first notification based on the first comparison result, wherein the third point in time is subsequent to the first point in time and prior to the second point in time, and providing the first notification at the third point in time. Platform 510 can facilitate in whole or in part obtaining data from a plurality of sensors associated with a machine, identifying a first level of alertness of a user of the machine in accordance with the data, predicting a first operation needed of the machine, wherein the first operation occurs subsequent to the identifying of the first level of alertness of the user, resulting in a predicted operation, identifying a second level of alertness required of the user to perform the predicted operation, responsive to determining that the user is insufficiently alert to perform the predicted operation in accordance with the first level of alertness and the second level of alertness: identifying a second operation to be performed in lieu of the first operation or in conjunction with the first operation, and responsive to determining that the user is sufficiently alert to perform the predicted operation in accordance with the first level of alertness and the second level of alertness: identifying a notification to provide to the user, resulting in an identified notification, and providing the identified notification to the user. Platform 510 can facilitate in whole or in part obtaining data from a plurality of sensors associated with a primary task at a first point in time, wherein a first user assists in a performance of the primary task, predicting an operation required of the first user to assist in the performance of the primary task at a second point in time that is subsequent to the first point in time, resulting in a predicted operation, determining at a third point in time that is subsequent to the first point in time and prior to the second point in time, that the first user is engaged in the primary task in an amount that is greater than a first threshold, and responsive to the determining that the first user is engaged in the primary task in an amount that is greater than the first threshold: identifying a notification to provide to the first user in relation to the predicted operation, and identifying a fourth point in time that is subsequent to the third point in time and prior to the second point in time, and providing the notification to the first user at the fourth point in time.

In one or more embodiments, the mobile network platform 510 can generate and receive signals transmitted and received by base stations or access points such as base station or access point 122. Generally, mobile network platform 510 can comprise components, e.g., nodes, gateways, interfaces, servers, or disparate platforms, that facilitate both packet-switched (PS) (e.g., internet protocol (IP), frame relay, asynchronous transfer mode (ATM)) and circuit-switched (CS) traffic (e.g., voice and data), as well as control generation for networked wireless telecommunication. As a non-limiting example, mobile network platform 510 can be included in telecommunications carrier networks, and can be considered carrier-side components as discussed elsewhere herein. Mobile network platform 510 comprises CS gateway node(s) 512 which can interface CS traffic received from legacy networks like telephony network(s) 540 (e.g., public switched telephone network (PSTN), or public land mobile network (PLMN)) or a signaling system #7 (SS7) network 560. CS gateway node(s) 512 can authorize and authenticate traffic (e.g., voice) arising from such networks. Additionally, CS gateway node(s) 512 can access mobility, or roaming, data generated through SS7 network 560; for instance, mobility data stored in a visited location register (VLR), which can reside in memory 530. Moreover, CS gateway node(s) 512 interfaces CS-based traffic and signaling and PS gateway node(s) 518. As an example, in a 3GPP UMTS network, CS gateway node(s) 512 can be realized at least in part in gateway GPRS support node(s) (GGSN). It should be appreciated that functionality and specific operation of CS gateway node(s) 512, PS gateway node(s) 518, and serving node(s) 516, is provided and dictated by radio technology(ies) utilized by mobile network platform 510 for telecommunication over a radio access network 520 with other devices, such as a radiotelephone 575.

In addition to receiving and processing CS-switched traffic and signaling, PS gateway node(s) 518 can authorize and authenticate PS-based data sessions with served mobile devices. Data sessions can comprise traffic, or content(s), exchanged with networks external to the mobile network platform 510, like wide area network(s) (WANs) 550, enterprise network(s) 570, and service network(s) 580, which can be embodied in local area network(s) (LANs), can also be interfaced with mobile network platform 510 through PS gateway node(s) 518. It is to be noted that WANs 550 and enterprise network(s) 570 can embody, at least in part, a service network(s) like IP multimedia subsystem (IMS). Based on radio technology layer(s) available in technology resource(s) or radio access network 520, PS gateway node(s) 518 can generate packet data protocol contexts when a data session is established; other data structures that facilitate routing of packetized data also can be generated. To that end, in an aspect, PS gateway node(s) 518 can comprise a tunnel interface (e.g., tunnel termination gateway (TTG) in 3GPP UMTS network(s) (not shown)) which can facilitate packetized communication with disparate wireless network(s), such as Wi-Fi networks.

In embodiment 500, mobile network platform 510 also comprises serving node(s) 516 that, based upon available radio technology layer(s) within technology resource(s) in the radio access network 520, convey the various packetized flows of data streams received through PS gateway node(s) 518. It is to be noted that for technology resource(s) that rely primarily on CS communication, server node(s) can deliver traffic without reliance on PS gateway node(s) 518; for example, server node(s) can embody at least in part a mobile switching center. As an example, in a 3GPP UMTS network, serving node(s) 516 can be embodied in serving GPRS support node(s) (SGSN).

For radio technologies that exploit packetized communication, server(s) 514 in mobile network platform 510 can execute numerous applications that can generate multiple disparate packetized data streams or flows, and manage (e.g., schedule, queue, format . . . ) such flows. Such application(s) can comprise add-on features to standard services (for example, provisioning, billing, customer support . . . ) provided by mobile network platform 510. Data streams (e.g., content(s) that are part of a voice call or data session) can be conveyed to PS gateway node(s) 518 for authorization/authentication and initiation of a data session, and to serving node(s) 516 for communication thereafter. In addition to application server, server(s) 514 can comprise utility server(s), a utility server can comprise a provisioning server, an operations and maintenance server, a security server that can implement at least in part a certificate authority and firewalls as well as other security mechanisms, and the like. In an aspect, security server(s) secure communication served through mobile network platform 510 to ensure network's operation and data integrity in addition to authorization and authentication procedures that CS gateway node(s) 512 and PS gateway node(s) 518 can enact. Moreover, provisioning server(s) can provision services from external network(s) like networks operated by a disparate service provider; for instance, WAN 550 or Global Positioning System (GPS) network(s) (not shown). Provisioning server(s) can also provision coverage through networks associated to mobile network platform 510 (e.g., deployed and operated by the same service provider), such as the distributed antennas networks shown in FIG. 1(*s*) that enhance wireless service coverage by providing more network coverage.

It is to be noted that server(s) 514 can comprise one or more processors configured to confer at least in part the functionality of mobile network platform 510. To that end, the one or more processor can execute code instructions stored in memory 530, for example. It is should be appreciated that server(s) 514 can comprise a content manager, which operates in substantially the same manner as described hereinbefore.

In example embodiment 500, memory 530 can store information related to operation of mobile network platform 510. Other operational information can comprise provisioning information of mobile devices served through mobile network platform 510, subscriber databases; application intelligence, pricing schemes, e.g., promotional rates, flat-rate programs, couponing campaigns; technical specification(s) consistent with telecommunication protocols for operation of disparate radio, or wireless, technology layers; and so forth. Memory 530 can also store information from at least one of telephony network(s) 540, WAN 550, SS7 network 560, or enterprise network(s) 570. In an aspect, memory 530 can be, for example, accessed as part of a data store component or as a remotely connected memory store.

In order to provide a context for the various aspects of the disclosed subject matter, FIG. 5, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules comprise routines, programs, components, data structures, etc. that perform particular tasks and/or implement particular abstract data types.

Figure 6:
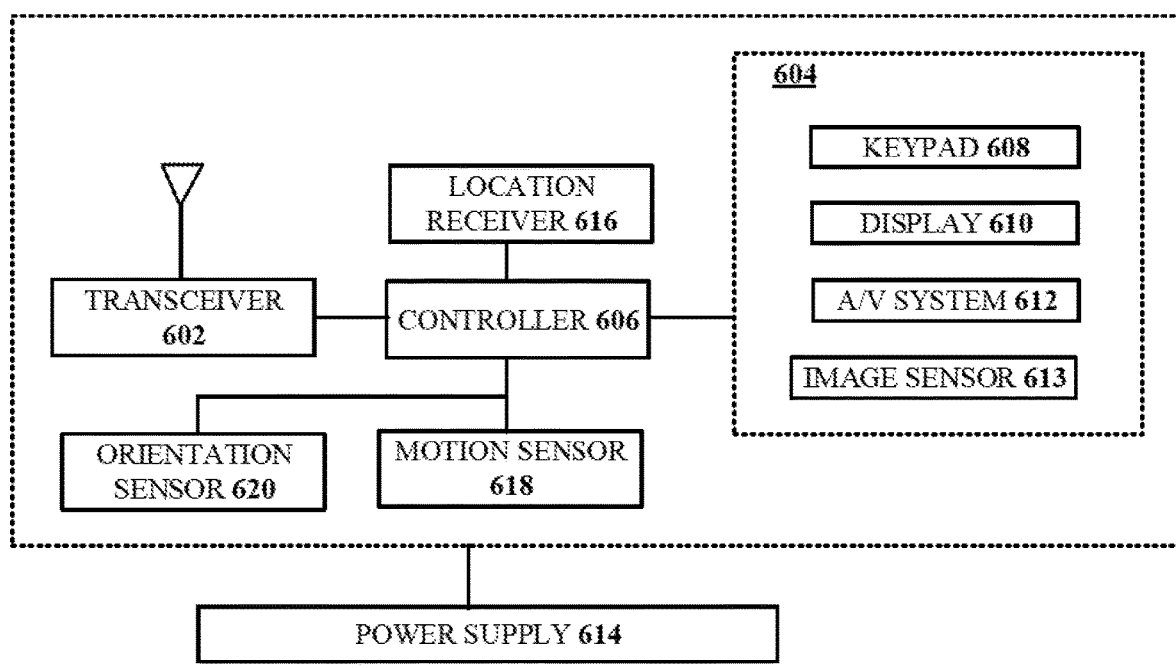
FIG. 6 is a block diagram of an example, non-limiting embodiment of a communication device in accordance with various aspects described herein.

Turning now to FIG. 6, an illustrative embodiment of a communication device 600 is shown. The communication device 600 can serve as an illustrative embodiment of devices such as data terminals 114, mobile devices 124, vehicle 126, display devices 144 or other client devices for communication via either communications network 125. For example, computing device 600 can facilitate in whole or in part obtaining data from a plurality of sensors at a first point in time, analyzing the data to identify a first level of alertness of a user, predicting a second level of alertness that is required by the user to operate a machine at a second point in time that is subsequent to the first point in time, comparing the first level of alertness to the second level of alertness to generate a first comparison result, identifying a first type of a first notification based on the first comparison result, identifying a third point in time to provide the first notification based on the first comparison result, wherein the third point in time is subsequent to the first point in time and prior to the second point in time, and providing the first notification at the third point in time. Computing device 600 can facilitate in whole or in part obtaining data from a plurality of sensors associated with a machine, identifying a first level of alertness of a user of the machine in accordance with the data, predicting a first operation needed of the machine, wherein the first operation occurs subsequent to the identifying of the first level of alertness of the user, resulting in a predicted operation, identifying a second level of alertness required of the user to perform the predicted operation, responsive to determining that the user is insufficiently alert to perform the predicted operation in accordance with the first level of alertness and the second level of alertness: identifying a second operation to be performed in lieu of the first operation or in conjunction with the first operation, and responsive to determining that the user is sufficiently alert to perform the predicted operation in accordance with the first level of alertness and the second level of alertness: identifying a notification to provide to the user, resulting in an identified notification, and providing the identified notification to the user. Computing device 600 can facilitate in whole or in part obtaining data from a plurality of sensors associated with a primary task at a first point in time, wherein a first user assists in a performance of the primary task, predicting an operation required of the first user to assist in the performance of the primary task at a second point in time that is subsequent to the first point in time, resulting in a predicted operation, determining at a third point in time that is subsequent to the first point in time and prior to the second point in time, that the first user is engaged in the primary task in an amount that is greater than a first threshold, and responsive to the determining that the first user is engaged in the primary task in an amount that is greater than the first threshold: identifying a notification to provide to the first user in relation to the predicted operation, and identifying a fourth point in time that is subsequent to the third point in time and prior to the second point in time, and providing the notification to the first user at the fourth point in time.

The communication device 600 can comprise a wireline and/or wireless transceiver 602 (herein transceiver 602), a user interface (UI) 604, a power supply 614, a location receiver 616, a motion sensor 618, an orientation sensor 620, and a controller 606 for managing operations thereof. The transceiver 602 can support short-range or long-range wireless access technologies such as Bluetooth®, ZigBee®, WiFi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 602 can also be adapted to support circuit-switched wireline access technologies (such as PSTN), packet-switched wireline access technologies (such as TCP/IP, VoIP, etc.), and combinations thereof.

The UI 604 can include a depressible or touch-sensitive keypad 608 with a navigation mechanism such as a roller ball, a joystick, a mouse, or a navigation disk for manipulating operations of the communication device 600. The keypad 608 can be an integral part of a housing assembly of the communication device 600 or an independent device operably coupled thereto by a tethered wireline interface (such as a USB cable) or a wireless interface supporting for example Bluetooth®. The keypad 608 can represent a numeric keypad commonly used by phones, and/or a QWERTY keypad with alphanumeric keys. The UI 604 can further include a display 610 such as monochrome or color LCD (Liquid Crystal Display), OLED (Organic Light Emitting Diode) or other suitable display technology for conveying images to an end user of the communication device 600. In an embodiment where the display 610 is touch-sensitive, a portion or all of the keypad 608 can be presented by way of the display 610 with navigation features.

The display 610 can use touch screen technology to also serve as a user interface for detecting user input. As a touch screen display, the communication device 600 can be adapted to present a user interface having graphical user interface (GUI) elements that can be selected by a user with a touch of a finger. The display 610 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 610 can be an integral part of the housing assembly of the communication device 600 or an independent device communicatively coupled thereto by a tethered wireline interface (such as a cable) or a wireless interface.

The UI 604 can also include an audio system 612 that utilizes audio technology for conveying low volume audio (such as audio heard in proximity of a human ear) and high volume audio (such as speakerphone for hands free operation). The audio system 612 can further include a microphone for receiving audible signals of an end user. The audio system 612 can also be used for voice recognition applications. The UI 604 can further include an image sensor 613 such as a charged coupled device (CCD) camera for capturing still or moving images.

The power supply 614 can utilize common power management technologies such as replaceable and rechargeable batteries, supply regulation technologies, and/or charging system technologies for supplying energy to the components of the communication device 600 to facilitate long-range or short-range portable communications. Alternatively, or in combination, the charging system can utilize external power sources such as DC power supplied over a physical interface such as a USB port or other suitable tethering technologies.

The location receiver 616 can utilize location technology such as a global positioning system (GPS) receiver capable of assisted GPS for identifying a location of the communication device 600 based on signals generated by a constellation of GPS satellites, which can be used for facilitating location services such as navigation. The motion sensor 618 can utilize motion sensing technology such as an accelerometer, a gyroscope, or other suitable motion sensing technology to detect motion of the communication device 600 in three-dimensional space. The orientation sensor 620 can utilize orientation sensing technology such as a magnetometer to detect the orientation of the communication device 600 (north, south, west, and east, as well as combined orientations in degrees, minutes, or other suitable orientation metrics).

The communication device 600 can use the transceiver 602 to also determine a proximity to a cellular, WiFi, Bluetooth®, or other wireless access points by sensing techniques such as utilizing a received signal strength indicator (RSSI) and/or signal time of arrival (TOA) or time of flight (TOF) measurements. The controller 606 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the communication device 600.

Other components not shown in FIG. 6 can be used in one or more embodiments of the subject disclosure. For instance, the communication device 600 can include a slot for adding or removing an identity module such as a Subscriber Identity Module (SIM) card or Universal Integrated Circuit Card (UICC). SIM or UICC cards can be used for identifying subscriber services, executing programs, storing subscriber data, and so on.

The terms "first," "second," "third," and so forth, as used in the claims, unless otherwise clear by context, is for clarity only and doesn't otherwise indicate or imply any order in time. For instance, "a first determination," "a second determination," and "a third determination," does not indicate or imply that the first determination is to be made before the second determination, or vice versa, etc.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can comprise both volatile and nonvolatile memory, by way of illustration, and not limitation, volatile memory, non-volatile memory, disk storage, and memory storage. Further, nonvolatile memory can be included in read only memory (ROM), programmable ROM (PROM), electrically programmable ROM (EPROM), electrically erasable ROM (EEPROM), or flash memory. Volatile memory can comprise random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, comprising single-processor or multiprocessor computer systems, mini-computing devices, mainframe computers, as well as personal computers, hand-held computing devices (e.g., PDA, phone, smartphone, watch, tablet computers, netbook computers, etc.), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

In one or more embodiments, information regarding use of services can be generated including services being accessed, media consumption history, user preferences, and so forth. This information can be obtained by various methods including user input, detecting types of communications (e.g., video content vs. audio content), analysis of content streams, sampling, and so forth. The generating, obtaining and/or monitoring of this information can be responsive to an authorization provided by the user. In one or more embodiments, an analysis of data can be subject to authorization from user(s) associated with the data, such as an opt-in, an opt-out, acknowledgement requirements, notifications, selective authorization based on types of data, and so forth.

Some of the embodiments described herein can also employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out various embodiments thereof. Moreover, the classifier can be employed to determine a ranking or priority of each cell site of the acquired network. A classifier is a function that maps an input attribute vector, x=(x1, x2, x3, x4, . . . , xn), to a confidence that the input belongs to a class, that is, f(x)=confidence (class). Such classification can employ a probabilistic and/or statistical-based analysis (e.g., factoring into the analysis utilities and costs) to determine or infer an action that a user desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches comprise, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via a observing UE behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to predetermined criteria which of the acquired cell sites will benefit a maximum number of subscribers and/or which of the acquired cell sites will add minimum value to the existing communication network coverage, etc.

As used in some contexts in this application, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device or computer-readable storage/communications media. For example, computer readable storage media can include, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms such as "user equipment," "mobile station," "mobile," subscriber station," "access terminal," "terminal," "handset," "mobile device" (and/or terms representing similar terminology) can refer to a wireless device utilized by a subscriber or user of a wireless communication service to receive or convey data, control, voice, video, sound, gaming or substantially any data-stream or signaling-stream. The foregoing terms are utilized interchangeably herein and with reference to the related drawings.

Furthermore, the terms "user," "subscriber," "customer," "consumer" and the like are employed interchangeably throughout, unless context warrants particular distinctions among the terms. It should be appreciated that such terms can refer to human entities or automated components supported through artificial intelligence (e.g., a capacity to make inference based, at least, on complex mathematical formalisms), which can provide simulated vision, sound recognition and so forth.

As employed herein, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of user equipment. A processor can also be implemented as a combination of computing processing units.

As used herein, terms such as "data storage," data storage," "database," and substantially any other information storage component relevant to operation and functionality of a component, refer to "memory components," or entities embodied in a "memory" or components comprising the memory. It will be appreciated that the memory components or computer-readable storage media, described herein can be either volatile memory or nonvolatile memory or can include both volatile and nonvolatile memory.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

As may also be used herein, the term(s) "operably coupled to", "coupled to", and/or "coupling" includes direct coupling between items and/or indirect coupling between items via one or more intervening items. Such items and intervening items include, but are not limited to, junctions, communication paths, components, circuit elements, circuits, functional blocks, and/or devices. As an example of indirect coupling, a signal conveyed from a first item to a second item may be modified by one or more intervening items by modifying the form, nature or format of information in a signal, while one or more elements of the information in the signal are nevertheless conveyed in a manner than can be recognized by the second item. In a further example of indirect coupling, an action in a first item can cause a reaction on the second item, as a result of actions and/or reactions in one or more intervening items.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

What is claimed is:

1. A device for managing tasks in accordance with alertness levels, comprising:
a processing system including a processor; and
a memory that stores executable instructions that, when executed by the processing system, facilitate performance of operations, the operations comprising:
obtaining data from a plurality of sensors at a first point in time;
analyzing the data to identify a first level of alertness of a user;
predicting a second level of alertness that is required by the user to operate a machine at a second point in time that is subsequent to the first point in time;
comparing the first level of alertness to the second level of alertness to generate a first comparison result;
identifying a first type of a first notification based on the first comparison result;
identifying a third point in time to provide the first notification based on the first comparison result, wherein the third point in time is subsequent to the first point in time and prior to the second point in time; and
providing the first notification at the third point in time.

2. The device of claim 1, wherein the plurality of sensors includes a microphone, and wherein the data includes an acoustic characteristic of the user as obtained by the microphone.

3. The device of claim 2, wherein the microphone is included in a mobile communication device associated with the user.

4. The device of claim 2, wherein the acoustic characteristic is associated with a communication session at least partially executed by a mobile communication device of the user.

5. The device of claim 1, wherein the data is based on a presentation of a media content item by the machine.

6. The device of claim 1, wherein the user is remotely located from the machine.

7. The device of claim 1, wherein the identifying of the first type of the first notification is further based on a profile of the user, and wherein the identifying of the third point in time is further based on the profile of the user.

8. The device of claim 1, wherein the operations further comprise:
obtaining second data from the plurality of sensors at a fourth point in time that is subsequent to the second point in time;
analyzing the second data to identify a third level of alertness of the user;
predicting a fourth level of alertness that is required by the user to operate the machine at a fifth point in time that is subsequent to the fourth point in time;
comparing the third level of alertness to the fourth level of alertness to generate a second comparison result;
identifying a second type of a second notification based on the second comparison result;
identifying a sixth point in time to provide the second notification based on the second comparison result, wherein the sixth point in time is subsequent to the fourth point in time and prior to the fifth point in time; and
providing the second notification at the sixth point in time.

9. The device of claim 8, wherein the operations further comprise:
recording a response of the user in connection with an operation of the machine to generate a recorded response.

10. The device of claim 9, wherein the identifying of the second type of the second notification is further based on the recorded response, and wherein the identifying of the sixth point in time is further based on the recorded response.

11. The device of claim 8, wherein the first type and the second type are different types.

12. The device of claim 1, wherein the operations further comprise:
obtaining second data from a second plurality of sensors, wherein a sensor included in the second plurality of sensors is associated with a second machine,
wherein the identifying of the first type of the first notification is further based on the second data.

13. The device of claim 12, wherein the identifying of the third point in time is further based on the second data.

14. The device of claim 12, wherein the operations further comprise:
obtaining a first response of the user, the machine, or a combination thereof, at a fourth point in time that is subsequent to the third point in time;
processing the first response to generate a suggestion for operating the machine, the second machine, or a combination thereof; and
providing the suggestion to the machine, the second machine, or the combination thereof.

15. A machine-readable medium, comprising executable instructions that, when executed by a processing system including a processor, facilitate performance of operations for managing tasks in accordance with alertness levels, the operations comprising:
obtaining data from a plurality of sensors;
identifying a first level of alertness of a user of a machine in accordance with the data;
predicting a first operation needed of the machine, wherein the first operation occurs subsequent to the identifying of the first level of alertness of the user, resulting in a predicted operation;
identifying a second level of alertness required of the user to perform the predicted operation;
responsive to determining that the user is insufficiently alert to perform the predicted operation in accordance with the first level of alertness and the second level of alertness:
identifying a second operation to be performed in lieu of the first operation or in conjunction with the first operation; and
responsive to determining that the user is sufficiently alert to perform the predicted operation in accordance with the first level of alertness and the second level of alertness:
identifying a notification to provide to the user, resulting in an identified notification; and
providing the identified notification to the user.

16. The machine-readable medium of claim 15, wherein the operations further comprise:
responsive to determining that the user is sufficiently alert to perform the predicted operation in accordance with the first level of alertness and the second level of alertness:
identifying a time when to provide the identified notification to the user, resulting in an identified time,
wherein the providing of the identified notification to the user comprises providing the identified notification at the identified time.

17. The machine-readable medium of claim 15, wherein the machine includes a vehicle, wherein the second operation is an automated operation that is performed by the vehicle without assistance of the user, wherein the second operation comprises re-routing the vehicle from a first route to a destination to a second route to the destination, and wherein the second route is different from the first route.

18. The machine-readable medium of claim 15, wherein the plurality of sensors include a first camera included in the machine and a second camera located along a route where the machine operates, wherein the data includes a first image captured by the first camera and a second image captured by the second camera, and wherein the predicting of the first operation is based on an analysis of the first image and the second image.

19. A method for managing tasks in accordance with alertness levels, comprising:
    obtaining, by a processing system including a processor, data from a plurality of sensors associated with a primary task at a first point in time, wherein a first user assists in a performance of the primary task;
    predicting, by the processing system, an operation required of the first user to assist in the performance of the primary task at a second point in time that is subsequent to the first point in time, resulting in a predicted operation;
    determining, by the processing system and at a third point in time that is subsequent to the first point in time and prior to the second point in time, that the first user is engaged in the primary task in an amount that is greater than a first threshold; and
    responsive to the determining that the first user is engaged in the primary task in an amount that is greater than the first threshold:
        identifying a notification to provide to the first user in relation to the predicted operation; and
        identifying a fourth point in time that is subsequent to the third point in time and prior to the second point in time; and
    providing the notification to the first user at the fourth point in time.

20. The method of claim 19, wherein the first user is located proximal to a machine, wherein the primary task includes operating the machine, wherein the machine includes a display device and a speaker, and wherein the method further comprises:
    identifying, by the processing system and in accordance with the data, that the first user is engaged in a secondary task during the primary task, wherein the secondary task includes:
        a communication session via a communication device,
        a discussion with a second user that is located proximal to the machine, a presentation of media via the display device, the speaker, or a combination thereof, or any combination thereof; and
    determining, by the processing system, a level of engagement of the first user in the secondary task in accordance with the identifying of the secondary task and in accordance with a profile of the first user,
    wherein the determining that the first user is engaged in the primary task in an amount that is greater than the first threshold is based on the determining of the level of engagement of the first user in the secondary task.

\* \* \* \* \*